US008404245B2

(12) United States Patent
Guss et al.

(10) Patent No.: US 8,404,245 B2
(45) Date of Patent: Mar. 26, 2013

(54) **IMMUNIZATION OF NON-HUMAN MAMMALS AGAINST *STREPTOCOCCUS EQUI***

(75) Inventors: Bengt Guss, Uppsala (SE); Jan-Ingmar Flock, Bromma (SE); Karin Jacobsson, Storvreta (SE); Kenneth Janzon, Hagersten (SE); Lars Frykberg, Storvreta (SE); Margareta Flock, Bromma (SE); Rune Bergman, Tumba (SE)

(73) Assignee: Intervacc AB, Hagersten (SE)

( * ) Notice: Subject to any disclaimer, the term of this patent is extended or adjusted under 35 U.S.C. 154(b) by 1546 days.

(21) Appl. No.: 10/530,879

(22) PCT Filed: Oct. 10, 2003

(86) PCT No.: PCT/SE03/01587
§ 371 (c)(1),
(2), (4) Date: Oct. 27, 2005

(87) PCT Pub. No.: WO2004/032957
PCT Pub. Date: Apr. 22, 2004

(65) Prior Publication Data
US 2006/0140980 A1 Jun. 29, 2006

Related U.S. Application Data

(60) Provisional application No. 60/417,660, filed on Oct. 11, 2002.

(51) Int. Cl.
*A61K 39/09* (2006.01)
(52) U.S. Cl. .................................................. 424/190.1
(58) Field of Classification Search .................. None
See application file for complete search history.

(56) References Cited

U.S. PATENT DOCUMENTS 5,583,014 A 12/1996 Brown et al.

FOREIGN PATENT DOCUMENTS

| WO | WO-87/00436 A1 | 1/1987 |
| WO | WO-95/07296 A1 | 3/1995 |
| WO | WO-98/01561 A1 | 1/1998 |
| WO | WO-00/37496 A1 | 6/2000 |

OTHER PUBLICATIONS

Jonas Lannergard et al., "CNE, a collagen-binding protein of *Streptococcus equi*", FEMS Microbiology Letters, vol. 222, 2003, pp. 69-74.
Hans Lindmark., "Acta Universitatis Agriculturae Sueciae, AGRARIA 139, Characterization of Adhesive Extracellular Proteins from *Streptococcus equi*", 1999, Doctoral thesis Swedish University of Agricultural Sciences, Uppsala, pp. 1-49.
Hans Lindmark et al., "Acta Universitatis Agriculturae Sueciae, AGRAIA 139, Characterization of Adhesive Extracellular Proteins from *Streptococcus equi*", 1999, The NH2-terminal half of protein FNZ binds fibroconectin and is secreted in *S. equi subsq. equi* but not in *subsq zooepidemicus*, Swedish University of Agricultural Sciences, Uppsala, pp. 1-13.
Hans Lindmark et al., "Pulsed-field gel electrophoresis and distribution of the genes *zag* and *fnz* in isolates of *Streptococcus equi*", Research in Veterinary Science, vol. 66, 1999, pp. 93-99.
Hans Lindmark et al., "SFS, a Novel Fibronectin-Binding Protein from *Streptococcus equi*, Inhibits the Binding between Fibronectin and Collagen" Infection and Immunity, vol. 67, No. 5 May 1999, pp. 2383-2388.
Han Lindmark et al., "Comparison of the Fibronectin-Binding Protein FNE from *Streptococcus equi* Subspecies *equi* with FNZ from *S. equi* Subspecies *zooepidemicus* Reveals a Major and Conserved Different", Infection and Immunity, vol. 67, No. 5, May 2001, pp. 3159-3163.
Harry S. Courtney et al., "Cloning, Sequencing, and Exprerssion of a Fibronectin/ Fibrinogen-Binding Protein from Group A Streptococci," Infection and Immunity, vol. 62, No. 9, Sep. 1994, pp. 3937-3946.
D. Cue et al., "*Streptoccus pyogenes* Serotype M1 Encodes Multiple Pathways for Entry into Human Epithelial Cells," Infection and Immunity, Oct. 1998, vol. 66, No. 10, pp. 4593-4601.
Jorge E. Galan et al., "Immunologic and Genetic Comparison of *Streptococcus equi* Isolates from the United States and Europe," vol. 26, No. 6, Jun. 1988, pp. 1142-1146.
Richard O. Hynes, "Fibronectins," Chapter 5, Interactions of Fibronectins, pp. 84-112.
Eva Engvall et al., "Affinity of Fibronectin to Collagensd of Different Genetic Types and to Fibrinogen," Downloaded from www.jem.org on Oct. 26, 2005, pp. 1584-1595.
Joseph M. Patti et al., "Molecular Characterization and Expression of a Gene Encoding a *Staphylococcus aureus* Collagen Adhesin," vol. 267, No. 7, Mar. 5, pp. 4766-4772, 1992.
Hans Jonsson et al., "A Protein G-Related Cell Surface Protein in *Streptococcus zooepidemicus*," Infection and Immunity, vol. 63, No. 8, Aug. 1995, pp. 2968-2975.
Hans Lindmark et al., "Fibronectin-Binding Protein of *Streptococcus equi* subsp. *zooepidemicus*," Infection and Immunity, Oct. 1996, pp. 3993-3999, vol. 64, No. 10.
Karin Jacobsson et al., "Shot-gun phage display mapping of two streptococcal cell-surface proteins", Microbiol.Res. (1997) 152. pp. 1-8.
Louis Winner III et al., "New Model for Analysis of Mucosal Immunity; Intestinal Secretion of Specific Monoclonal Immunoglobulin A from Hybridoma Tumors Protects against *Vibrio cholerae* Infection," Infection and Immunity, Mar. 1991, pp. 977-982, vol. 59, No. 3.
Emanuel Hanski et al., "Protein F, a fibronectin-binding protein, is an adhesin of the group A streptococcus *Streptococcus pyogenes*," Proc. Natl. Acad. Sci. USA, vol. 89, pp. 6172-6176, Jul. 1992.

(Continued)

*Primary Examiner* — Brian J Gangle
(74) *Attorney, Agent, or Firm* — Birch, Stewart, Kolasch & Birch, LLP.

(57) ABSTRACT

The present invention is concerned with an antigenic composition comprising at least one antigen that comprises at least one antigenic epitope or antigenic determinant derived from a protein present in one or both of *S. equi* subsp. *Equi* and subsp. *Zooepidemicus* and use thereof for immunization of non-human mammals against *S. equi* subsp. *equi* and/or subsp. *Zooepidemicus*. The present invention also discloses a vaccine composition comprising the aforesaid antigenic composition as immunizing component. The antigens used are EAG, FNZ, SFS, SEC and ScLC.

20 Claims, 19 Drawing Sheets

OTHER PUBLICATIONS

Emanuel Hanski et al., "Expression of Protein F, the Fibronectin-Binding Protein of *Streptococcus pygenes* JRS4, in Heterologous Streptococcal and Enterococcal Strains Promotes Their Adherence to Respiratory Epithelial Cells," Infection and Immuntiy, Dec. 1992, pp. 5119-5125, vol. 60, No. 12.

Gabriella Molinari et al., "The Fibronectin -Binding Protein of *Streptococcus pyogenes*, Sfbl, Is Involved in the Internalization of Group A Streptococci by Epithelial Cells," Infection and Immunity, Apr. 1997, pp. 1357-1363, vol. 65, No. 4.

Hans Lindmark, Characterization of adhesive extracellular proteins from *Streptococcus equi*, Doctors dissertation, ISSN 1401-6249, ISBN 91-576-5488-3, pp. 7-49 (1999).

Hans Lindmark et al., The $NH_2$-terminal half of protein FNZ binds fibronectin and is secreted in *S. equi* subsp. *equi* but not in subsp. *zooepidemicus*, Department of Microbiology, Swedish University of Agricultural Sciences, S-750-07, Uppsala, Sweden, pp. 1-13.

Hans Lindmark, Research in Veterinary Science, vol. 66, pp. 93-99 (1999).

http://www.horseandhound.co.uk/news/397/72788.html, Goodwill Payout for Strangles-Infected Yard (Jan. 9, 2006).

M. Flock et al., Vaccine, vol. 24, pp. 4144-4151 (2006).

Andrew Waller et al., Vaccination of Horses Against Strangles Using Recombinant Antigens from *Streptococcus equi*, Animal Health Trust, Newmarket UK; Microbiology and Tumorbiology Center, Karolinska Institutet, Stockholm; Department of Microbiology, Swedish University of Agricultural Sciences, Uppsala; Nordvacc Lakemedel AB, Stockholm, Sweden, Mar. 10, 2006.

Asa Karlstrom et al., Veterinary Microbiology, vol. 114, pp. 72-81 (2006).

IgG antibodies against SFSC1, 2 weeks after intranasal inoculation with Streptococcus equi subsp. equi

IgG antibodies against FNZN after subcutaneous immunization with FNZN, SFSC1 o EAG4B

Fig 8

BAL/NW IgA antibodies against SFSC1 after intranasal immunization with FNZN, SFSC1 and EAG4B

SEQUENCE LISTING

<160> NUMBER OF SEQ ID NOS: 28

<210> SEQ ID NO 1
<211> LENGTH: 180
<212> TYPE: PRT
<213> ORGANISM: Streptococcus equi

<400> SEQUENCE: 1

```
Met Ala Leu Asp Ala Thr Thr Val Leu Glu Pro Thr Thr Ala Phe Ile
1               5                   10                  15

Arg Glu Ala Val Arg Glu Ile Asn Gln Leu Ser Asp Asp Tyr Ala Asp
            20                  25                  30

Asn Gln Glu Leu Gln Ala Val Leu Ala Asn Ala Gly Val Glu Ala Leu
        35                  40                  45

Ala Ala Asp Thr Val Asp Gln Ala Lys Ala Leu Asp Lys Ala Lys
    50                  55                  60

Ala Ala Val Ala Gly Val Gln Leu Asp Glu Ala Arg Arg Glu Ala Tyr
65              70                  75                  80

Arg Thr Ile Asn Ala Leu Ser Asp Gln His Lys Ser Gln Lys Val
                85                  90                  95

Gln Leu Ala Leu Val Ala Ala Ala Ala Lys Val Ala Asp Ala Ala Ser
            100                 105                 110

Val Asp Gln Val Asn Ala Ala Ile Asn Asp Ala His Thr Ala Ile Ala
        115                 120                 125

Asp Ile Thr Gly Ala Ala Leu Leu Glu Ala Lys Glu Ala Ile Asn
    130                 135                 140

Glu Leu Lys Gln Tyr Gly Ile Ser Asp Tyr Tyr Val Thr Leu Ile Asn
145                 150                 155                 160

Lys Ala Lys Thr Val Glu Gly Val Asn Ala Leu Lys Ala Lys Ile Leu
                165                 170                 175

Ser Ala Leu Pro
            180

<210> SEQ ID NO 2
<211> LENGTH: 597
<212> TYPE: PRT
<213> ORGANISM: Streptococcus equi

<400> SEQUENCE: 2

Met Lys Thr Lys Ser Phe Arg Lys Val Leu Thr Thr Ser Ala Thr Cys
1               5                   10                  15

Ile Val Leu Ala Thr Ser Phe Ala Gly Gly Thr Leu Arg Val Trp Ala
            20                  25                  30

Glu Gln Leu Tyr Tyr Gly Trp Asn Asp Gly Thr Arg Gln Ser Ser Pro
        35                  40                  45

Tyr Phe Leu Tyr Val Ser Pro Lys Asn Ala Pro Lys Arg Glu Leu Lys
    50                  55                  60

Asp Glu Tyr Val Val Tyr Cys Phe Asn Lys Lys Leu Tyr Trp Pro Asp
65              70                  75                  80

Gln Trp Glu Ser Ile Tyr Ser Asn Phe Asn Asp Ile Arg Ser Pro Tyr
                85                  90                  95

Asn Asp Leu Pro Val Tyr Glu Lys Lys Leu Gly Tyr Asp Gly Ile Phe
            100                 105                 110

Lys Gln Tyr Ala Pro Asp Tyr Lys Lys Asp Ile Ser Asp Ile Ala Ser
        115                 120                 125

Ala Leu Val Ala Val Leu Ser Asn Gly Tyr Pro Thr Asn Lys Ser Gln
    130                 135                 140

Leu Ser Thr Ser Tyr His Leu Asn Asn Asp Ser Ser Arg Lys Val Thr
145                 150                 155                 160

Gln Leu Ala Ile Trp Tyr Phe Ser Asp Ser Leu Thr Lys Glu Tyr Leu
                165                 170                 175

Lys Asp Thr Gly Gly Tyr Asn Leu Asn Asp Met Glu Lys Lys Ala Leu
            180                 185                 190
```

-continued

```
Asp Phe Leu Ile Ser Lys Gly Glu Asp Ser Lys Leu Lys Ser Glu Gln
        195                 200                 205

Ser Asn Tyr Ser Leu Asp Ile Tyr Val Tyr Gln Ser Gly Gly His Asp
    210                 215                 220

His Met Lys Asp Tyr Gln Asn Leu Leu Gly Ser Thr Leu Ile Pro Lys
225                 230                 235                 240

Glu Pro Leu Lys Pro Gln Leu Gly Gly Phe Ser Gly His Asn Gly Asn
                245                 250                 255

Gly Leu Ser Gly Leu Glu Gly Gly Ser Gly Ser Gln Glu Thr Asn
            260                 265                 270

Glu Asp Gly Lys Lys Gly Leu Ile Gly Phe His Gly Leu Ser Gly
    275                 280                 285

Ser Glu Gly Lys Arg Asp Pro Leu Pro Gly Leu Lys Gly Glu Ala Gly
    290                 295                 300

Ala Pro Asp Thr Pro Gln Lys Pro Asn Asp Pro Leu Gln Gly Leu Glu
305                 310                 315                 320

Gly Gly Asn Ser Pro Ile Val Glu Gln Asn Tyr Gly Ser Thr Glu Gly
                325                 330                 335

Tyr His Gly Gln Ser Gly Ile Leu Glu Glu Thr Glu Asp Thr Asn Pro
            340                 345                 350

Pro Gly Ile Ile Leu Gly Gly Ser Gly Asn Val Glu Thr His Glu Asp
        355                 360                 365

Thr Arg Asn Pro His Leu Met Gly Ile Gly Gly Leu Ala Gly Glu
370                 375                 380

Ser Gly Glu Thr Thr Pro Lys Pro Gly Gln Thr Gly Gln Gly Pro
385                 390                 395                 400

Val Ile Glu Thr Thr Glu Asp Thr Gln Lys Gly Met Ser Gly Gln Ser
                405                 410                 415

Gly Gly Thr Ile Glu Ser Glu Asn Thr Lys Lys Pro Glu Val Met Ile
            420                 425                 430

Gly Gly Gln Gly Gln Thr Ile Glu Thr Thr Glu Asp Thr Gln Lys Gly
        435                 440                 445

Met Ser Gly Gln Ser Gly Gly Thr Ile Glu Ser Glu Asp Thr Lys Lys
    450                 455                 460

Pro Glu Val Met Ile Gly Gly Gln Gly Gln Ile Ile Asp Phe Ser Glu
465                 470                 475                 480

Asn Thr Gln Ser Gly Met Ser Gly Gln Ser Gly Asp Thr Thr Val Ile
                485                 490                 495

Glu Asp Thr Lys Lys Ser Glu Ile Ile Ile Gly Gln Gly Gln Ile
            500                 505                 510

Ile Asp Phe Ser Glu Asp Thr Gln Pro Gly Met Ser Gly Gln Ser Gly
        515                 520                 525

Gly Thr Thr Ile Val Glu Asp Thr Lys Lys Pro Thr Pro Lys Pro Lys
    530                 535                 540

Pro Ala Pro Ala Pro Ile Val Asn Asp Glu Lys Pro Asn Lys Gly Thr
545                 550                 555                 560

His Leu Pro Gln Thr Ser Asp Met Lys Gln Leu Thr Leu Ser Ile Ile
                565                 570                 575

Gly Ala Met Ser Met Leu Leu Val Leu Cys Leu Ser Leu Phe Lys Arg
            580                 585                 590

Pro Ser Lys Lys Asp
        595
```

<210> SEQ ID NO 3

<211> LENGTH: 371
<212> TYPE: PRT
<213> ORGANISM: Streptococcus equi

<400> SEQUENCE: 3

```
Met Arg Lys Thr Glu Gly Arg Phe Arg Thr Trp Lys Ser Lys Lys Gln
1               5                   10                  15

Trp Leu Phe Ala Gly Ala Val Val Thr Ser Leu Leu Leu Gly Ala Ala
            20                  25                  30

Leu Val Phe Gly Gly Leu Leu Gly Ser Leu Gly Gly Ser Ser His Gln
            35                  40                  45

Ala Arg Pro Lys Glu Gln Pro Val Ser Ser Ile Gly Asp Asp Lys
        50                  55                  60

Ser His Lys Ser Ser Ser Asp Ser Met Val Ser Arg Pro Pro Lys Lys
65                  70                  75                  80

Asp Asn Leu Gln Pro Lys Pro Ser Asp Gln Pro Thr Asn His Gln His
                85                  90                  95

Gln Ala Thr Ser Pro Ser Gln Pro Thr Ala Lys Ser Ser Gly His His
            100                 105                 110

Gly Asn Gln Pro Gln Ser Leu Ser Val Asn Ser Gln Gly Asn Ser Ser
        115                 120                 125

Gly Gln Ala Ser Glu Pro Gln Ala Ile Pro Asn Gln Gly Pro Ser Gln
    130                 135                 140

Pro Leu Gly Leu Arg Gly Gly Asn Ser Ser Gly Ser Gly His His His
145                 150                 155                 160

Gln Pro Gln Gly Lys Pro Gln His Leu Asp Leu Gly Lys Asp Asn Ser
                165                 170                 175

Ser Pro Gln Pro Gln Pro Lys Pro Gln Gly Asn Ser Pro Lys Leu Pro
            180                 185                 190

Glu Lys Gly Leu Asn Gly Glu Asn Gln Lys Glu Pro Glu Gln Gly Glu
        195                 200                 205

Arg Gly Glu Ala Gly Pro Pro Leu Ser Gly Leu Ser Gly Asn Asn Gln
    210                 215                 220

Gly Arg Pro Ser Leu Pro Gly Leu Asn Gly Glu Asn Gln Lys Glu Pro
225                 230                 235                 240

Glu Gln Gly Glu Arg Gly Glu Ala Gly Pro Pro Ser Thr Pro Asn Leu
                245                 250                 255

Glu Gly Asn Asn Arg Lys Asn Pro Leu Lys Gly Leu Asp Gly Glu Asn
            260                 265                 270

Lys Pro Lys Glu Asp Leu Asp Gly Lys Gly Leu Ser Gly Glu Asn Asp
        275                 280                 285

Glu Ser Pro Lys Leu Lys Asp Glu His Pro Tyr Asn His Gly Arg Arg
    290                 295                 300

Asp Gly Tyr Arg Val Gly Tyr Glu Asp Gly Tyr Gly Gly Lys Lys His
305                 310                 315                 320

Lys Gly Asp Tyr Pro Lys Arg Phe Asp Glu Ser Ser Pro Lys Glu Tyr
                325                 330                 335

Asn Asp Tyr Ser Gln Gly Tyr Asn Asp Asn Tyr Gly Asn Gly Tyr Leu
            340                 345                 350

Asp Gly Leu Ala Asp Arg Gly Gly Lys Arg Gly Tyr Gly Tyr Ser Tyr
        355                 360                 365

Asn Pro Asp
    370
```

<210> SEQ ID NO 4

<211> LENGTH: 657
<212> TYPE: PRT
<213> ORGANISM: Streptococcus equi

<400> SEQUENCE: 4

```
Leu Lys Gln Leu Thr Lys Ile Val Ser Val Leu Leu Val Phe
1               5                   10                  15

Thr Leu Ser Ala Ser Leu His Lys Val Arg Ala Thr Asn Leu Ser Asp
                20                  25                  30

Asn Ile Thr Ser Leu Thr Val Ala Ser Ser Leu Arg Asp Gly Glu
                35                  40                  45

Arg Thr Thr Val Lys Val Ala Phe Asp Asp Lys Lys Gln Lys Ile Lys
    50                  55                  60

Ala Gly Asp Thr Ile Glu Val Thr Trp Pro Thr Ser Gly Asn Val Tyr
65                  70                  75                  80

Ile Gln Gly Phe Asn Lys Thr Ile Pro Leu Asn Ile Arg Gly Val Asp
                85                  90                  95

Val Gly Thr Leu Glu Val Thr Leu Asp Lys Ala Val Phe Thr Phe Asn
            100                 105                 110

Gln Asn Ile Glu Thr Met His Asp Val Ser Gly Trp Gly Glu Phe Asp
            115                 120                 125

Ile Thr Val Arg Asn Val Thr Gln Thr Thr Ala Glu Thr Ser Gly Thr
            130                 135                 140

Thr Thr Val Lys Val Gly Asn Arg Thr Ala Thr Ile Thr Val Thr Lys
145                 150                 155                 160

Pro Glu Ala Gly Thr Gly Thr Ser Ser Phe Tyr Tyr Lys Thr Gly Asp
                165                 170                 175

Met Gln Pro Asn Asp Thr Glu Arg Val Arg Trp Phe Leu Leu Ile Asn
            180                 185                 190

Asn Asn Lys Glu Trp Val Ala Asn Thr Val Thr Val Glu Asp Asp Ile
            195                 200                 205

Gln Gly Gly Gln Thr Leu Asp Met Ser Ser Phe Asp Ile Thr Val Ser
            210                 215                 220

Gly Tyr Arg Asn Glu Arg Phe Val Gly Glu Asn Ala Leu Thr Glu Phe
225                 230                 235                 240

His Thr Thr Phe Pro Asn Ser Val Ile Thr Ala Thr Asp Asn His Ile
                245                 250                 255

Ser Val Arg Leu Asp Gln Tyr Asp Ala Ser Gln Asn Thr Val Asn Ile
            260                 265                 270

Ala Tyr Lys Thr Lys Ile Thr Asp Phe Asp Gln Lys Glu Phe Ala Asn
            275                 280                 285

Asn Ser Lys Ile Trp Tyr Gln Ile Leu Tyr Lys Asp Gln Val Ser Gly
            290                 295                 300

Gln Glu Ser Asn His Gln Val Ala Asn Ile Asn Ala Asn Gly Gly Val
305                 310                 315                 320

Asp Gly Ser Arg Tyr Thr Ser Phe Thr Val Lys Lys Ile Trp Asn Asp
                325                 330                 335

Lys Glu Asn Gln Asp Gly Lys Arg Pro Lys Thr Ile Thr Val Gln Leu
            340                 345                 350

Tyr Ala Asn Asp Gln Lys Val Asn Asp Lys Thr Ile Glu Leu Ser Asp
            355                 360                 365

Thr Asn Ser Trp Gln Ala Ser Phe Gly Lys Leu Asp Lys Tyr Asp Ser
            370                 375                 380

Gln Asn Gln Lys Ile Thr Tyr Ser Val Lys Glu Val Met Val Pro Val
385                 390                 395                 400
```

Gly Tyr Gln Ser Gln Val Glu Gly Asp Ser Gly Val Gly Phe Thr Ile
                405                 410                 415

Thr Asn Thr Tyr Thr Pro Glu Val Ile Ser Ile Thr Gly Gln Lys Thr
            420                 425                 430

Trp Asp Asp Arg Glu Asn Gln Asp Gly Lys Arg Pro Lys Glu Ile Thr
        435                 440                 445

Val Arg Leu Leu Ala Asn Asp Ala Ala Thr Asp Lys Val Ala Thr Ala
450                 455                 460

Ser Glu Gln Thr Gly Trp Lys Tyr Thr Phe Thr Asn Leu Pro Lys Tyr
465                 470                 475                 480

Lys Asp Gly Lys Gln Ile Thr Tyr Thr Ile Gln Glu Asp Pro Val Ala
                485                 490                 495

Asp Tyr Thr Thr Thr Ile Gln Gly Phe Asp Ile Thr Asn His His Glu
            500                 505                 510

Val Ala Leu Thr Ser Leu Lys Val Ile Lys Val Trp Asn Asp Lys Asp
        515                 520                 525

Asp Tyr Tyr His Lys Arg Pro Lys Glu Ile Thr Ile Leu Leu Lys Ala
530                 535                 540

Asp Gly Lys Val Ile Arg Glu His Gln Met Thr Pro Asp Gln Gln Gly
545                 550                 555                 560

Lys Trp Glu Tyr Thr Phe Asp Gln Leu Pro Val Tyr Gln Thr Gly Lys
                565                 570                 575

Lys Ile Ser Tyr Ser Ile Glu Glu Lys Gln Val Ala Gly Tyr Gln Ala
            580                 585                 590

Pro Val Tyr Glu Val Asp Glu Gly Leu Lys Gln Val Thr Val Thr Asn
        595                 600                 605

Thr Leu Asn Pro Ser Tyr Lys Leu Pro Asp Thr Gly Gly Gln Gly Val
    610                 615                 620

Lys Trp Tyr Leu Leu Ile Gly Gly Gly Phe Ile Ile Val Ala Ile Leu
625                 630                 635                 640

Val Leu Ile Ser Leu Tyr Gln Lys His Lys Arg His Asn Met Ser Lys
                645                 650                 655

Pro

<210> SEQ ID NO 5
<211> LENGTH: 34
<212> TYPE: DNA
<213> ORGANISM: Artificial Sequence
<220> FEATURE:
<223> OTHER INFORMATION: OZAG43B primer used to PCR-amplify a
      DNA-fragment corresponding to amino acid residues 34-262 in
      protein EAG

<400> SEQUENCE: 5
ttttctcgag ctacggtaga gctgataaaa tctc                              34

<210> SEQ ID NO 6
<211> LENGTH: 32
<212> TYPE: DNA
<213> ORGANISM: Artificial Sequence
<220> FEATURE:
<223> OTHER INFORMATION: OZAG15 primer used to PCR-amplify a
      DNA-fragment corresponding to amino acid residues 34-262 in
      protein EAG

<400> SEQUENCE: 6
tcagccatgg ctctagatgc tacaacggtg tt                                32

<210> SEQ ID NO 7
<211> LENGTH: 600
<212> TYPE: DNA
<213> ORGANISM: Streptococcus equi

<400> SEQUENCE: 7

```
aaataattttt gtttaacttt aagaaggaga tataaccatg gctctagatg ctacaacggt      60
gttagagcct acaacagcct tcattagaga agctgttagg gaaatcaatc agctgagtga     120
tgactacgct gacaatcaag agcttcaggc tgttcttgct aatgctggag ttgaggcact     180
tgctgcagat actgttgatc aggctaaagc agctcttgac aaagcaaagg cagctgttgc     240
tggtgttcag cttgatgaag caagacgtga ggcttacaga acaatcaatg ccttaagtga     300
tcagcacaaa agcgatcaaa aggttcagct agctctagtt gctgcagcag ctaaggtggc     360
agatgctgct tcagttgatc aagtgaatgc agccattaat gatgctcata cagctattgc     420
ggacattaca ggagcagcct tgttggaggc taaagaagct gctatcaatg aactaaagca     480
gtatggcatt agtgattact atgtgacctt aatcaacaaa gccaaaactg ttgaaggtgt     540
caatgcgctt aaggcaaaga ttttatcagc tctaccgtag ctcgagcccg ggtgctttgc     600
```

<210> SEQ ID NO 8
<211> LENGTH: 30
<212> TYPE: DNA
<213> ORGANISM: Artificial Sequence
<220> FEATURE:
<223> OTHER INFORMATION: OSFS25 primer used to PCR amplify the 3' end of the sfs gene

<400> SEQUENCE: 8

```
ggtcccatgg caactccgaa tttagaagga                                        30
```

<210> SEQ ID NO 9
<211> LENGTH: 29
<212> TYPE: DNA
<213> ORGANISM: Artificial Sequence
<220> FEATURE:
<223> OTHER INFORMATION: OSFS23 primer used to PCR amplify the 3' end of the sfs gene

<400> SEQUENCE: 9

```
cagactcgag gtcgggattg taagaatag                                         29
```

<210> SEQ ID NO 10
<211> LENGTH: 125
<212> TYPE: PRT
<213> ORGANISM: Streptococcus equi

<400> SEQUENCE: 10

```
Met Ala Thr Pro Asn Leu Glu Gly Asn Asn Arg Lys Asn Pro Leu Lys
  1               5                  10                  15
Gly Leu Asp Gly Glu Asn Lys Pro Lys Glu Asp Leu Asp Gly Lys Gly
             20                  25                  30
Leu Ser Gly Glu Asn Asp Glu Ser Pro Lys Leu Lys Asp Glu His Pro
         35                  40                  45
Tyr Asn His Gly Arg Arg Asp Gly Tyr Arg Val Gly Tyr Glu Asp Gly
     50                  55                  60
Tyr Gly Gly Lys Lys His Lys Gly Asp Tyr Pro Lys Arg Phe Asp Glu
 65                  70                  75                  80
Ser Ser Pro Lys Glu Tyr Asn Asp Tyr Ser Gln Gly Tyr Asn Asp Asn
                 85                  90                  95
Tyr Gly Asn Gly Tyr Leu Asp Gly Leu Ala Asp Arg Gly Gly Lys Arg
```

```
                    100                 105                 110
Gly Tyr Gly Tyr Ser Tyr Asn Pro Asp Leu Glu Pro Gly
            115                 120                 125

<210> SEQ ID NO 11
<211> LENGTH: 34
<212> TYPE: DNA
<213> ORGANISM: Artificial Sequence
<220> FEATURE:
<223> OTHER INFORMATION: Forward primer OFNZ1 used to construct the
      clone pT2fnzN

<400> SEQUENCE: 11
accatggcta gcgcagagca gctttattat gggt                                  34

<210> SEQ ID NO 12
<211> LENGTH: 32
<212> TYPE: DNA
<213> ORGANISM: Artificial Sequence
<220> FEATURE:
<223> OTHER INFORMATION: Reverse primer OFNZ2 used to construct the
      clone pT2fnzN

<400> SEQUENCE: 12
atacccggga tatccttcgg tactaccata gt                                    32

<210> SEQ ID NO 13
<211> LENGTH: 310
<212> TYPE: PRT
<213> ORGANISM: Streptococcus equi

<400> SEQUENCE: 13

Met Ala Ser Ala Glu Gln Leu Tyr Tyr Gly Trp Asn Asp Gly Thr Arg
1               5                   10                  15

Gln Ser Ser Pro Tyr Phe Leu Tyr Val Ser Pro Lys Asn Ala Pro Lys
            20                  25                  30

Arg Glu Leu Lys Asp Glu Tyr Val Val Tyr Cys Phe Asn Lys Lys Leu
        35                  40                  45

Tyr Trp Pro Asp Gln Trp Glu Ser Ile Tyr Ser Asn Phe Asn Asp Ile
50                  55                  60

Arg Ser Pro Tyr Asn Asp Leu Pro Val Tyr Glu Lys Lys Leu Gly Tyr
65                  70                  75                  80

Asp Gly Ile Phe Lys Gln Tyr Ala Pro Asp Tyr Lys Lys Asp Ile Ser
                85                  90                  95

Asp Ile Ala Ser Ala Leu Val Ala Val Leu Ser Asn Gly Tyr Pro Thr
            100                 105                 110

Asn Lys Ser Gln Leu Ser Thr Ser Tyr His Leu Asn Asn Asp Ser Ser
        115                 120                 125

Arg Lys Val Thr Gln Leu Ala Ile Trp Tyr Phe Ser Asp Ser Leu Thr
130                 135                 140

Lys Glu Tyr Leu Lys Asp Thr Gly Gly Tyr Asn Leu Asn Asp Met Glu
145                 150                 155                 160

Lys Lys Ala Leu Asp Phe Leu Ile Ser Lys Gly Glu Asp Ser Lys Leu
                165                 170                 175

Lys Ser Glu Gln Ser Asn Tyr Ser Leu Asp Ile Tyr Val Tyr Gln Ser
            180                 185                 190

Gly Gly His Asp His Met Lys Asp Tyr Gln Asn Leu Leu Gly Ser Thr
        195                 200                 205

Leu Ile Pro Lys Glu Pro Leu Lys Pro Gln Leu Gly Gly Phe Ser Gly
210                 215                 220
```

```
His Asn Gly Asn Gly Leu Ser Gly Leu Glu Gly Ser Ser Gly Ser
225                 230                 235                 240

Gln Glu Thr Asn Glu Asp Gly Lys Lys Gly Leu Ile Gly Phe His Gly
            245                 250                 255

Gly Leu Ser Gly Ser Glu Gly Lys Arg Asp Pro Leu Pro Gly Leu Lys
            260                 265                 270

Gly Glu Ala Gly Ala Pro Asp Thr Pro Gln Lys Pro Asn Asp Pro Leu
            275                 280                 285

Gln Gly Leu Glu Gly Gly Asn Ser Pro Ile Val Glu Gln Asn Tyr Gly
            290                 295                 300

Ser Thr Glu Gly Tyr Gly
305                 310

<210> SEQ ID NO 14
<211> LENGTH: 5
<212> TYPE: PRT
<213> ORGANISM: Streptococcus equi

<400> SEQUENCE: 14

Leu Pro Asp Thr Gly
1               5

<210> SEQ ID NO 15
<211> LENGTH: 1971
<212> TYPE: DNA
<213> ORGANISM: Streptococcus equi

<400> SEQUENCE: 15
ttgaaacaac tgacaaagat cgttagtgtg gtcttgttgc tggtctttac ccttagtgct      60
agcctgcaca aggttcgggc aactaatctt agtgacaaca tcacatcatt gacggttgct     120
tcttcatcac tccgagatgg agagagaacg acggtaaagg ttgcgtttga tgacaaaaaa     180
cagaaaatca aggcagggga tacgatagag gtcacctggc ctacaagtgg taatgtctac     240
attcagggct ttaataaaac cataccgctt aatattagag gggtagatgt tggtaccttg     300
gaggtcacgc tagacaaggc tgttttcaca ttcaatcaaa atattgaaac aatgcatgat     360
gtctctggtt ggggagagtt tgatattact gttagaaatg tgacacaaac caccgctgaa     420
acatcaggaa cgaccacagt aaaggtaggc aatcgcactg ctactatcac tgttactaag     480
cctgaggcag gcactggtac cagctcattt tattataaga ctggtgatat gcagcccaat     540
gatactgagc gtgtgagatg gttcctgctg attaacaaca caaggaatg ggtggccaat     600 actgttacag tcgaagacga tattcaaggt ggtcaaacct tggatatgag cagctttgac     660
atcaccgtat ctggttatcg taacgagcgc ttcgttgggg aaaacgctct gacagagttt     720
catacaacat ttccaaattc tgtcattacg gcaacagata tcacattag tgtgcggtta     780 gatcaatatg atgcctcaca aaacactgtc aacattgctt ataagacaaa gataacggac     840
tttgaccaaa aagaatttgc caacaacagt aaaatctggt accagatttt atacaaggat     900
caggtatcgg gtcaagagtc aaaccaccaa gtagccaata tcaatgctaa cggcggggtt     960
gatggcagtc gctataccag ctttactgtc aagaaaattt ggaatgacaa ggaaaatcaa    1020
gacggtaagc gtccaaagac tattactgtt cagctttacg ccaatgatca gaaagttaat    1080
gataagacca ttgaattgag tgatactaat agctggcaag caagtttttgg taagctggat    1140 aagtatgaca gtcagaacca aaaaattacc tacagtgtca aggaagtgat ggttcctgtt    1200
ggctaccaat cgcaggttga gggggatagt ggagtaggat ttaccattac caacacctat    1260
```

```
acaccagagg tcattagcat taccggtcaa aaaacttggg acgacaggga aaaccaagac    1320
ggtaaacgtc ctaaggagat tacgttcgt ttattggcaa atgacgctgc aactgacaag     1380
gtagcaactg cttcagagca aaccggctgg aagtatacat ttaccaatct accgaaatac    1440
aaagatggta aacagatcac ctacacgatc caagaggacc ctgtggcaga ttacaccaca    1500
accattcagg gatttgatat taccaatcat catgaggtag ccttgaccag cctaaaggtc    1560
atcaaggttt ggaatgataa ggacgattat taccataaac gtcccaagga gattaccatt    1620
ttgctaaagg cagatggcaa ggtgattcgt gaacatcaga tgacaccgga tcagcaagga    1680
aaatgggaat acacctttga ccagctgccg gtctatcaga caggcaagaa aatcagctac    1740
agcattgagg aaaaacaggt tgctggctat caagcccctg tctatgaggt tgatgaaggc    1800
ttgaagcagg tcactgtaac caacacccct aacccaagct acaagctgcc tgacaccgga    1860
ggacaaggag tgaaatggta cctgttaatc ggtggcggtt ttatcatcgt cgcaatcctt    1920
gtactgatca gcctttatca aaacacaag cgccataaca tgtcaaaacc a             1971
```

<210> SEQ ID NO 16
<211> LENGTH: 32
<212> TYPE: DNA
<213> ORGANISM: Artificial Sequence
<220> FEATURE:
<223> OTHER INFORMATION: OSEC1:5 primer used to PCR-amplify a
      DNA-fragment corresponding to a sequence from amino acid no. 27
      to amino acid no. 615 in protein SEC (SEQ. ID. NO: 4)

<400> SEQUENCE: 16

```
catgccatgg caactaatct tagtgacaac at                                   32
```

<210> SEQ ID NO 17
<211> LENGTH: 32
<212> TYPE: DNA
<213> ORGANISM: Artificial Sequence
<220> FEATURE:
<223> OTHER INFORMATION: OSEC3:3 primer used to PCR-amplify a
      DNA-fragment corresponding to a sequence from amino acid no. 27
      to amino acid no. 615 in protein SEC (SEQ. ID. NO: 4)

<400> SEQUENCE: 17

```
ccgctcgagc ttgtagcttg ggttaagggt gt                                   32
```

<210> SEQ ID NO 18
<211> LENGTH: 32
<212> TYPE: DNA
<213> ORGANISM: Artificial Sequence
<220> FEATURE:
<223> OTHER INFORMATION: OSEC2:3 primer used to PCR-amplify a
      DNA-fragment corresponding to a sequence from amino acid no. 27
      to amino acid no. 328 in protein SEC (SEQ. ID. NO: 4)

<400> SEQUENCE: 18

```
ccgctcgaga aagctggtat agcgactgcc at                                   32
```

<210> SEQ ID NO 19
<211> LENGTH: 1782
<212> TYPE: DNA
<213> ORGANISM: Streptococcus equi

<400> SEQUENCE: 19

```
atggcaacta atcttagtga caacatcaca tcattgacgg ttgcttcttc atcactccga    60
gatggagaga gaacgacggt aaaggttgcg tttgatgaca aaaaacagaa atcaaggca     120 ggggatacga tagaggtcac ctggcctaca agtggtaatg tctacattca gggctttaat    180
```

```
aaaaccatac cgcttaatat tagaggggta gatgttggta ccttggaggt cacgctagac    240
aaggctgttt tcacattcaa tcaaatatat gaaacaatgc atgatgtctc tggttgggga    300
gagtttgata ttactgttag aaatgtgaca caaaccaccg ctgaaacatc aggaacgacc    360
acagtaaagg taggcaatcg cactgctact atcactgtta ctaagcctga ggcaggcact    420
ggtaccagct cattttatta taagactggt gatattcagc ccaatgatac tgagcgtgtg    480
agatggttcc tgctgattaa caacaacaag gaatgggtgg ccaatactgt tacagtcgaa    540
gacgatattc aaggtggtca aaccttggat atgagcagct ttgacatcac cgtatctggt    600
tatcgtaacg agcgcttcgt tggggaaaac gctctgacag agtttcatac aacatttcca    660
aattctgtca ttacggcaac agataatcac attagtgtgc ggttagatca atatgatgcc    720
tcacaaaaca ctgtcaacat tgcttataag acaaagataa cggactttga ccaaaaagaa    780
tttgccaaca acagtaaaat ctggtaccag attttataca aggatcaggt atcgggtcaa    840
gagtcaaacc accaagtagc caatatcaat gctaacggcg gggttgatgg cagtcgctat    900
accagcttta ctgtcaagaa aatttggaat gacaaggaaa atcaagacgg taagcgtcca    960
aagactatta ctgttcagct ttcgccaat gatcagaaag ttaatgataa gaccattgaa   1020
ttgagtgata ctaatagctg gcaagcaagt tttggtaagc tggataagta tgacagtcag   1080
aaccaaaaaa ttacctacag tgtcaaggaa gtgatggttc ctgttggcta ccaatcgcag   1140
gttgaggggg atagtggagt aggatttacc attaccaaca cctatacacc agaggtcatt   1200
agcattaccg gtcaaaaaac ttgggacgac agggaaaacc aagacggtaa acgtcctaag   1260
gagattacgg ttcgtttatt ggcaaatgac gctgcaactg caaggtagc aactgcttca   1320
gagcaaaccg gctggaagta tacatttacc aatctaccga aatacaaaga tggtaaacag   1380
atcacctaca cgatccaaga ggaccctgtg gcagattaca ccacaaccat tcagggattt   1440
gatattccca atcatcatga ggtagccttg accagcctaa aggtcatcaa ggtttggaat   1500
gataaggacg attattacca taaacgtccc aaggagatta ccattttgct aaaggcagat   1560
ggcaaggtga ttcgtgaaca tcagatgaca ccggatcagc aaggaaaatg gaatacacc    1620
tttgaccagc tgccggtcta tcaggcaggc aagaaaatca gctacagcat tgaggaaaaa   1680
caggttgctg ctatcaagc ccctgtctat gaggttgatg aaggcttgaa gcaggtcact   1740
gtaaccaaca cccttaaccc aagctacaag ctcgagcccg gg                      1782
```

<210> SEQ ID NO 20
<211> LENGTH: 594
<212> TYPE: PRT
<213> ORGANISM: Streptococcus equi

<400> SEQUENCE: 20

```
Met Ala Thr Asn Leu Ser Asp Asn Ile Thr Ser Leu Thr Val Ala Ser
1               5                   10                  15

Ser Ser Leu Arg Asp Gly Glu Arg Thr Thr Val Lys Val Ala Phe Asp
                20                  25                  30

Asp Lys Lys Gln Lys Ile Lys Ala Gly Asp Thr Ile Glu Val Thr Trp
            35                  40                  45

Pro Thr Ser Gly Asn Val Tyr Ile Gln Gly Phe Asn Lys Thr Ile Pro
        50                  55                  60

Leu Asn Ile Arg Gly Val Asp Val Gly Thr Leu Glu Val Thr Leu Asp
65                  70                  75                  80

Lys Ala Val Phe Thr Phe Asn Gln Asn Ile Glu Thr Met His Asp Val
                85                  90                  95
```

-continued

```
Ser Gly Trp Gly Glu Phe Asp Ile Thr Val Arg Asn Val Thr Gln Thr
            100                 105                 110

Thr Ala Glu Thr Ser Gly Thr Thr Val Lys Val Gly Asn Arg Thr
        115                 120                 125

Ala Thr Ile Thr Val Thr Lys Pro Glu Ala Gly Thr Gly Thr Ser Ser
130                 135                 140

Phe Tyr Tyr Lys Thr Gly Asp Ile Gln Pro Asn Asp Thr Glu Arg Val
145                 150                 155                 160

Arg Trp Phe Leu Leu Ile Asn Asn Lys Glu Trp Val Ala Asn Thr
                165                 170                 175

Val Thr Val Glu Asp Asp Ile Gln Gly Gln Thr Leu Asp Met Ser
        180                 185                 190

Ser Phe Asp Ile Thr Val Ser Gly Tyr Arg Asn Glu Arg Phe Val Gly
        195                 200                 205

Glu Asn Ala Leu Thr Glu Phe His Thr Thr Phe Pro Asn Ser Val Ile
210                 215                 220

Thr Ala Thr Asp Asn His Ile Ser Val Arg Leu Asp Gln Tyr Asp Ala
225                 230                 235                 240

Ser Gln Asn Thr Val Asn Ile Ala Tyr Lys Thr Lys Ile Thr Asp Phe
            245                 250                 255

Asp Gln Lys Glu Phe Ala Asn Asn Ser Lys Ile Trp Tyr Gln Ile Leu
            260                 265                 270

Tyr Lys Asp Gln Val Ser Gly Gln Glu Ser Asn His Gln Val Ala Asn
        275                 280                 285

Ile Asn Ala Asn Gly Gly Val Asp Gly Ser Arg Tyr Thr Ser Phe Thr
290                 295                 300

Val Lys Lys Ile Trp Asn Asp Lys Glu Asn Gln Asp Gly Lys Arg Pro
305                 310                 315                 320

Lys Thr Ile Thr Val Gln Leu Tyr Ala Asn Asp Gln Lys Val Asn Asp
            325                 330                 335

Lys Thr Ile Glu Leu Ser Asp Thr Asn Ser Trp Gln Ala Ser Phe Gly
            340                 345                 350

Lys Leu Asp Lys Tyr Asp Ser Gln Asn Gln Lys Ile Thr Tyr Ser Val
        355                 360                 365

Lys Glu Val Met Val Pro Val Gly Tyr Gln Ser Gln Val Glu Gly Asp
370                 375                 380

Ser Gly Val Gly Phe Thr Ile Thr Asn Thr Tyr Thr Pro Glu Val Ile
385                 390                 395                 400

Ser Ile Thr Gly Gln Lys Thr Trp Asp Asp Arg Glu Asn Gln Asp Gly
            405                 410                 415

Lys Arg Pro Lys Glu Ile Thr Val Arg Leu Leu Ala Asn Asp Ala Ala
        420                 425                 430

Thr Asp Lys Val Ala Thr Ala Ser Glu Gln Thr Gly Trp Lys Tyr Thr
        435                 440                 445

Phe Thr Asn Leu Pro Lys Tyr Lys Asp Gly Lys Gln Ile Thr Tyr Thr
        450                 455                 460

Ile Gln Glu Asp Pro Val Ala Asp Tyr Thr Thr Thr Ile Gln Gly Phe
465                 470                 475                 480

Asp Ile Thr Asn His His Glu Val Ala Leu Thr Ser Leu Lys Val Ile
            485                 490                 495

Lys Val Trp Asn Asp Lys Asp Tyr Tyr His Lys Arg Pro Lys Glu
            500                 505                 510

Ile Thr Ile Leu Leu Lys Ala Asp Gly Lys Val Ile Arg Glu His Gln
        515                 520                 525
```

Met Thr Pro Asp Gln Gln Gly Lys Trp Glu Tyr Thr Phe Asp Gln Leu
            530                 535                 540

Pro Val Tyr Gln Ala Gly Lys Lys Ile Ser Tyr Ser Ile Glu Glu Lys
545                 550                 555                 560

Gln Val Ala Gly Tyr Gln Ala Pro Val Tyr Glu Val Asp Glu Gly Leu
                565                 570                 575

Lys Gln Val Thr Val Thr Asn Thr Leu Asn Pro Ser Tyr Lys Leu Glu
            580                 585                 590

Pro Gly

<210> SEQ ID NO 21
<211> LENGTH: 921
<212> TYPE: DNA
<213> ORGANISM: Streptococcus equi

<400> SEQUENCE: 21

```
atggcaacta atcttagtga caacatcaca tcattgacgg ttgcttcttc atcactccga      60
gatggagaga gaacgacggt aaaggttgcg tttgatgaca aaaaacagaa atcaaggca     120
ggggatacga tagaggtcac ctggcctaca agtggtaatg tctacattca gggctttaat    180
aaaaccatac cgcttaatat tagaggggta gatgttggta ccttggaggt cacgctagac    240
aaggctgttt tcacattcaa tcaaaatatt gaaacaatgc atgatgtctc tggttgggga    300
gagtttgata ttactgttag aaatgtgaca caaccaccg ctgaaacatc aggaacgacc     360
acagtaaagg taggcaatcg cactgctact atcactgtta ctaagcctga ggcaggcact    420
ggtaccagct cattttatta taagactggt gatatgcagc ccaatgatac tgagcgtgtg    480
agatggttcc tgctgattaa caacaacaag gaatgggtgg ccaatactgt tacagtcgaa    540
gacgatattc aaggtggtca aaccttggat atgagcagct ttgacatcac cgtatctggt    600
tatcgtaacg agcgcttcgt tggggaaaac gctctgacag agtttcatac aacatttcca    660
aattctgtca ttacggcaac agataatcac attagtgtgc ggttagatca aatgatgcc     720
tcacaaaaca ctgtcaacat tgcttataag acaaagataa cggactttga ccaaaaagaa    780
tttgccaaca acagtaaaat ctggtaccag attttataca aggatcaggt atcgggtcaa    840
gagtcaaacc accaagtagc caatatcaat gctaacggcg gggttgatgg cagtcgctat    900
accagctttc tcgagcccgg g                                              921
```

<210> SEQ ID NO 22
<211> LENGTH: 307
<212> TYPE: PRT
<213> ORGANISM: Streptococcus equi

<400> SEQUENCE: 22

Met Ala Thr Asn Leu Ser Asp Asn Ile Thr Ser Leu Thr Val Ala Ser
1               5                   10                  15

Ser Ser Leu Arg Asp Gly Glu Arg Thr Thr Val Lys Val Ala Phe Asp
            20                  25                  30

Asp Lys Lys Gln Lys Ile Lys Ala Gly Asp Thr Ile Glu Val Thr Trp
        35                  40                  45

Pro Thr Ser Gly Asn Val Tyr Ile Gln Gly Phe Asn Lys Thr Ile Pro
    50                  55                  60

Leu Asn Ile Arg Gly Val Asp Val Gly Thr Leu Glu Val Thr Leu Asp
65                  70                  75                  80

Lys Ala Val Phe Thr Phe Asn Gln Asn Ile Glu Thr Met His Asp Val
                85                  90                  95

```
Ser Gly Trp Gly Glu Phe Asp Ile Thr Val Arg Asn Val Thr Gln Thr
            100                 105                 110

Thr Ala Glu Thr Ser Gly Thr Thr Val Lys Val Gly Asn Arg Thr
        115                 120                 125

Ala Thr Ile Thr Val Thr Lys Pro Glu Ala Gly Thr Gly Thr Ser Ser
130                 135                 140

Phe Tyr Tyr Lys Thr Gly Asp Met Gln Pro Asn Asp Thr Glu Arg Val
145                 150                 155                 160

Arg Trp Phe Leu Leu Ile Asn Asn Lys Glu Trp Val Ala Asn Thr
                165                 170                 175

Val Thr Val Glu Asp Asp Ile Gln Gly Gln Thr Leu Asp Met Ser
            180                 185                 190

Ser Phe Asp Ile Thr Val Ser Gly Tyr Arg Asn Glu Arg Phe Val Gly
        195                 200                 205

Glu Asn Ala Leu Thr Glu Phe His Thr Thr Phe Pro Asn Ser Val Ile
210                 215                 220

Thr Ala Thr Asp Asn His Ile Ser Val Arg Leu Asp Gln Tyr Asp Ala
225                 230                 235                 240

Ser Gln Asn Thr Val Asn Ile Ala Tyr Lys Thr Lys Ile Thr Asp Phe
                245                 250                 255

Asp Gln Lys Glu Phe Ala Asn Asn Ser Lys Ile Trp Tyr Gln Ile Leu
            260                 265                 270

Tyr Lys Asp Gln Val Ser Gly Gln Glu Ser Asn His Gln Val Ala Asn
        275                 280                 285

Ile Asn Ala Asn Gly Gly Val Asp Gly Ser Arg Tyr Thr Ser Phe Leu
290                 295                 300

Glu Pro Gly
305

<210> SEQ ID NO 23
<211> LENGTH: 302
<212> TYPE: PRT
<213> ORGANISM: Streptococcus equi

<400> SEQUENCE: 23

Met Thr Asn Lys Thr Lys Arg Thr Gly Leu Val Arg Lys Tyr Gly Ala
1               5                   10                  15

Cys Ser Ala Ala Ile Ala Leu Ala Ala Leu Ala Ser Leu Gly Ala Gly
            20                  25                  30

Lys Ala Val Lys Ala Asp Gln Pro Ala Ala Leu Lys Tyr Pro Glu Pro
        35                  40                  45

Arg Asp Tyr Phe Leu His Thr Arg Glu Gly Asp Val Ile Tyr Asp Glu
50                  55                  60

Asp Ile Lys Arg Tyr Phe Glu Asp Leu Glu Ala Tyr Leu Thr Ala Arg
65                  70                  75                  80

Leu Gly Gly Ile Asp Lys Lys Val Glu Glu Ala Ala Gln Lys Pro Gly
                85                  90                  95

Ile Pro Gly Pro Thr Gly Pro Gln Gly Pro Lys Gly Asp Lys Gly Asp
            100                 105                 110

Pro Gly Ala Pro Gly Glu Arg Gly Pro Ala Gly Pro Lys Gly Asp Thr
        115                 120                 125

Gly Glu Ala Gly Pro Arg Gly Glu Gln Gly Pro Ala Gly Gln Ala Gly
130                 135                 140

Glu Arg Gly Pro Lys Gly Asp Pro Gly Ala Pro Gly Pro Lys Gly Glu
145                 150                 155                 160
```

```
Lys Gly Asp Thr Gly Ala Val Gly Pro Lys Gly Glu Lys Gly Asp Thr
            165                 170                 175

Gly Ala Thr Gly Pro Lys Gly Asp Lys Gly Glu Arg Gly Glu Lys Gly
        180                 185                 190

Glu Gln Gly Gln Arg Gly Glu Lys Gly Glu Gln Gly Gln Arg Gly Glu
    195                 200                 205

Lys Gly Glu Gln Lys Pro Lys Gly Asp Gln Gly Lys Asp Thr Lys Pro
210                 215                 220

Ser Ala Pro Lys Ala Pro Glu Lys Ala Pro Pro Lys Ala Pro Lys
225                 230                 235                 240

Ala Ser Glu Gln Ser Ser Asn Pro Lys Ala Pro Ala Pro Lys Ser Ala
            245                 250                 255

Pro Ser Lys Ser Ala Ala Pro Thr Gly Gln Lys Ala Ala Leu Pro Ala
        260                 265                 270

Thr Gly Glu Ile Asn His Pro Phe Phe Thr Leu Ala Ala Leu Ser Val
    275                 280                 285

Ile Ala Ser Val Gly Val Leu Thr Leu Lys Gly Lys Lys Asp
290                 295                 300
```

<210> SEQ ID NO 24
<211> LENGTH: 909
<212> TYPE: DNA
<213> ORGANISM: Streptococcus equi

<400> SEQUENCE: 24

```
atgacaaaca aaacaaagcg tacaggattg gtacgcaagt acggtgcctg ctcagcagct      60
atcgccttag cagctcttgc aagcctggga gcaggtaaag cagtaaaggc agaccagcca     120
gcagcactaa aatatccaga acctagagac tattttcttc atactcgtga aggtgatgtt     180
atttatgatg aggatataaa aagatatttt gaggatttag aagcctattt aacagctaga     240
cttggtggga ttgataaaaa agtagaagaa gctgcccaaa agccaggtat tccaggtcct     300
actggccctc aaggtcctaa gggagacaaa ggagatccag gtgcccctgg tgagcgcggt     360
ccagctggac caagggcga tacgggcgaa gccggaccaa gaggtgagca aggcccagcc     420
ggacaagctg gagaacgtgg accaaaagga gatccaggtg ctccaggtcc taaaggtgaa     480
aagggtgata ctggtgcagt tggtcctaaa ggtgaaaaag gtgataccgg agcaaccgga     540
ccaaagggag acaagggcga acgcggtgaa aaaggcgagc aaggccaacg tggcgaaaaa     600
ggcgagcaag ccaacgcggt gaaaaaggc gagcaaaaac caagggtga tcaaggaaaa      660 gatacaaaac catcagctcc aaaagcacct gaaaaggctc ctgcaccaaa agctccaaag     720
gcttcagagc agtcatctaa tcctaaagca ccagctccta gtcagcacc aagcaaatca      780 gcggcaccaa caggtcaaaa agcagcccta ccagcaacag gggaaatcaa ccacccattc     840
ttcacccttg cagctcttag tgtcatcgct agcgtaggcg tcctaactct aaaaggaaaa     900
aaagactaa                                                            909
```

<210> SEQ ID NO 25
<211> LENGTH: 33
<212> TYPE: DNA
<213> ORGANISM: Artificial Sequence
<220> FEATURE:
<223> OTHER INFORMATION: OSCL2:5 primer used to PCR-amplify a
       DNA-fragment corresponding to amino acid 38 to amino acid 269
       in protein SclC

<400> SEQUENCE: 25

```
catgccatgg accagccagc agcactaaaa tat                                33
```

<210> SEQ ID NO 26
<211> LENGTH: 31
<212> TYPE: DNA
<213> ORGANISM: Artificial Sequence
<220> FEATURE:
<223> OTHER INFORMATION: OSCL3:3 primer used to PCR-amplify a
      DNA-fragment corresponding to amino acid 38 to amino acid 269
      in protein SclC

<400> SEQUENCE: 26

```
ccgctcgagg gctgctttt gacctgttgg t                                  31
```

<210> SEQ ID NO 27
<211> LENGTH: 237
<212> TYPE: PRT
<213> ORGANISM: Streptococcus equi

<400> SEQUENCE: 27

```
Met Asp Gln Pro Ala Ala Leu Lys Tyr Pro Glu Pro Arg Asp Tyr Phe
1               5                   10                  15

Leu His Thr Arg Glu Gly Asp Val Ile Tyr Asp Glu Asp Ile Lys Arg
            20                  25                  30

Tyr Phe Glu Asp Leu Glu Ala Tyr Leu Thr Ala Arg Leu Gly Gly Ile
        35                  40                  45

Asp Lys Lys Val Glu Glu Ala Ala Gln Lys Pro Gly Ile Pro Gly Pro
    50                  55                  60

Thr Gly Pro Gln Gly Pro Lys Gly Asp Lys Gly Asp Pro Gly Ala Pro
65                  70                  75                  80

Gly Glu Arg Gly Pro Ala Gly Pro Lys Gly Asp Thr Gly Glu Ala Gly
                85                  90                  95

Pro Arg Gly Glu Gln Gly Pro Ala Gly Gln Ala Gly Glu Arg Gly Pro
            100                 105                 110

Lys Gly Asp Pro Gly Ala Pro Gly Pro Lys Gly Glu Lys Gly Asp Thr
        115                 120                 125

Gly Ala Val Gly Pro Lys Gly Glu Lys Gly Asp Thr Gly Ala Thr Gly
    130                 135                 140

Pro Lys Gly Asp Lys Gly Glu Arg Gly Glu Lys Gly Glu Gln Gly Gln
145                 150                 155                 160

Arg Gly Glu Lys Gly Glu Gln Gly Gln Arg Gly Glu Lys Gly Glu Gln
                165                 170                 175

Lys Pro Lys Gly Asp Gln Gly Lys Asp Thr Lys Pro Ser Ala Pro Lys
            180                 185                 190

Ala Pro Glu Lys Ala Pro Ala Pro Lys Ala Pro Lys Ala Ser Glu Gln
        195                 200                 205

Ser Ser Asn Pro Lys Ala Pro Ala Pro Lys Ser Ala Pro Ser Lys Ser
    210                 215                 220

Ala Ala Pro Thr Gly Gln Lys Ala Ala Leu Glu Pro Gly
225                 230                 235
```

<210> SEQ ID NO 28
<211> LENGTH: 5
<212> TYPE: PRT
<213> ORGANISM: Artificial Sequence
<220> FEATURE:
<223> OTHER INFORMATION: Motif corresponding to the LPDTG motif (SEQ.
      ID. NO: 14) of the SEC protein
<220> FEATURE:
<221> NAME/KEY: misc_feature
<222> LOCATION: (3)..(3)

```
<223> OTHER INFORMATION: Xaa can be any naturally occurring amino acid

<400> SEQUENCE: 28

Leu Pro Xaa Thr Gly
1               5
```

IMMUNIZATION OF NON-HUMAN MAMMALS AGAINST *STREPTOCOCCUS EQUI*

This National Phase PCT application claims priority under 35 U.S.C. 119(e) on U.S. Provisional Application No(s). 60/417,660 filed on Oct. 11, 2002, the entire contents of which are hereby incorporated by reference.

BACKGROUND OF THE INVENTION

1. Field of the Invention

This invention is generally related to antigenic compositions and use thereof for immunization of non-human mammals, e.g. horses, against *Streptococcus equi*.

Streptococcal infections in horses are mainly caused by the species *Streptococcus equi*, which is classified as a Lancefield Group C *Streptococcus* and comprises two subspecies designated *equi* and *zooepidemicus*, respectively.

*Streptococcus equi* subsp. *equi*, which is virtually confined to horses, is the causative agent of strangles, a world-wide distributed and highly contagious serious disease of the upper respiratory tract of the Equidae. Strangles is one of the most frequently reported equine diseases world-wide and is characterized by fever, nasal discharge, and abscess formation in the retropharyngeal and mandibular lymph nodes. In some cases the disease shows a metastatic course in the body, so called "bastard strangles". The disease has a world-wide distribution and causes great economic losses. Moreover, since strangles is a highly contagious disease, not only infected animals but also all other members of e.g. an afflicted stud must be isolated for as long as up to three months.

*S. equi* subsp. *zooepidemicus* is considered as an opportunistic commensal often occurring in the upper respiratory tract of healthy horses. However, after stress or virus infection, it can cause a secondary infection, which results in strangles-like symptoms. Moreover, subsp. *zooepidemicus* infects not only horses but also a wide range of other animals, like pigs, dogs, cats, and cows. Even human cases of infection due to subsp. *zooepidemicus* have been reported. This subspecies has been implicated as the primary pathogen in conditions such as endometritis, cervicitis, abortion, mastitis, pneumonia, abscesses and joint infections.

Although it is possible to treat and cure these streptococcal infections with antibiotics, such as penicillin, tetracycline or gentamicin, an effective prophylactic agent that could prevent outbursts of such infections and obviate or reduce the risk for development of resistant strains associated with antibiotic treatment, would be appreciated.

2. Description of the Related Art

However, although many attempts have been made to develop prophylactic agents such as vaccines against *S. equi*, at the present time no efficient vaccines or immunizing preparations are available, neither for the subspecies *equi* nor for the subspecies *zooepidemicus*.

Existing vaccines against strangles are based on inactivated, e.g. heat-killed, or attenuated strains of *S. equi* subsp. *equi* or acid extracts/mutanolysin enriched in M-protein(s), i.e. immunogenic protein(s) produced by *S. equi*. A vaccine against *S. equi* subsp. *zooepidemicus* based on an M-like protein is disclosed in U.S. Pat. No. 5,583,014. In WO 87/00436, an avirulent strain of *S. equi* is disclosed for use as a vaccine against *S. equi* that stimulates an antibody response in the nasopharyngeal mucosa after administration thereof to a horse.

Since the previously developed vaccines or immunizing preparations are hampered by side-effects and, moreover, provide insufficient protection, there is a need for efficient and safe prophylactic agents, such as vaccines, that protect against *S. equi* infections and/or prevent spread thereof without giving rise to undesirable side-effects.

It is well known that attachment to eukaryotic cell surfaces is an essential step in the establishment of infection and colonization by bacterial pathogens. Accordingly, streptococcal surface proteins, that interact with and/or bind to different components of the Extracellular Matrix (ECM) or plasma proteins of the host cell, are potential candidates for use as active component(s) for immunizing purposes.

This is illustrated by the vaccines based on M-like proteins mentioned above or disclosed in the literature, i.e., WO 98/01561. The binding of fibrinogen and complement factor H to M-proteins is assumed to be important for the ability of streptococci to resist phagocytosis by polymorphonuclear leucocytes.

Another mechanism used by streptococci for attachment to host cells involves binding to the ECM component fibronectin (Fn) (Ref. 21, 22). Binding between Fn-binding bacterial cell-surface proteins and immobilized Fn promotes internalization of streptococci by epithelial cells (Ref. 2, 23, 24). Fibronectin is a dimeric glycoprotein found both in plasma and in a fibrillar form in the extracellular matrix. The main function of Fn is to mediate substrate adhesion of eukaryotic cells, which involves the binding of specific cell-surface receptors to certain domains of the Fn molecule. Furthermore, it also interacts with several other macromolecules, such as DNA, heparin, fibrin, and collagen.

Accordingly, Fn-binding proteins from different streptococcal species have been cloned and sequenced previously. For instance, from *S. equi*, one Fn-binding protein has been cloned and characterized, which is a Fn-binding cell-surface protein of subsp. *zooepidemicus*, that has been designated FNZ (Lindmark et al., 1996, Ref. 9). Another Fn-binding protein from *S. equi* subsp. *equi*, has been cloned and characterized by Lindmark and Guss (1999) (Ref. 12). This latter protein that is designated SFS and its potential use as an active component in a vaccine for protection of horses against strangles are disclosed in WO 00/37496.

In Jonsson et al. (1995) (Ref. 8), a protein designated ZAG has been cloned and characterized from *S. equi* subsp. *zooepidemicus* that mediates binding to the plasma proteinase inhibitor $\alpha_2 M$. It is speculated therein that this protein is similar in function to streptococcal M proteins. This protein, ZAG, is also disclosed in WO 95/07296, where its $\alpha_2 M$-binding properties are indicated. However, immunogenic properties or potential use thereof as an active component in a vaccine for protection of e.g. horses against strangles are not disclosed therein. The gene zag encoding ZAG is also disclosed in these references.

A gene that is similar to the aforesaid zag gene from *S. equi* subsp. *zooepidemicus* but is present in subsp. *equi* has been described by Lindmark et al. (1999) (Ref. 11) and Lindmark (1999) (Ref. 13). This gene is hereafter designated eag and encodes a protein designated EAG.

BRIEF SUMMARY OF THE INVENTION

The present invention is based on an antigenic composition comprising at least one antigen that comprises at least one antigenic epitope or antigenic determinant derived from a protein present in one or both of *S. equi* subsp. *equi* and subsp. *zooepidemicus* and use thereof for immunization of non-human mammals against *S. equi* subsp. *equi* and/or subsp. *zooepidemicus*.

The present invention is also directed to a vaccine composition comprising the afore-said antigenic composition as immunizing component, methods to prepare said antigenic or vaccine composition, methods to induce an immune response against *S. equi* in non-human mammals and methods for prophylactic or therapeutic treatment of *S. equi* infection in non-human mammals. When used generally, the expression "*S. equi*" refers to one or both of subsp. *equi* and subsp. *zooepidemicus*.

According to a suitable embodiment, the present invention is directed to a vaccine that protects equines, such as horses, against strangles.

In the context of infections caused by *S. equi* subsp. *equi*, the expression "non-human mammals" primarily refers to animals belonging to the family Equidae that consists of horses, donkeys and zebras and to hybrids thereof, such as mules and hinnies.

In connection with infections caused by *S. equi* subsp. *zooepidemicus*, the expression "non-human mammals" in addition refers also to other mammals such as cows, pigs, dogs and cats.

BRIEF DESCRIPTION OF THE DRAWINGS

In the following, the present invention is described in closer detail with reference to the drawings, where FIG. 1 shows IgG antibodies developed against FNZN in eight individual mice after intranasal inoculation with *Streptococcus equi* subsp. *equi*.

FIG. 2 shows IgG antibodies developed against SFSC1 in eight individual mice after intranasal inoculation with *Streptococcus equi* subsp. *equi*.

FIG. 3 shows IgG antibodies developed against EAG4B in eight individual mice after intranasal inoculation with *Streptococcus equi* subsp. *equi*.

FIG. 4 shows IgG antibodies developed in mice against FNZN after subcutaneous immunization with FNZN, SFSC1, and EAG4B. Results obtained for seven immunized mice and one non-immunized (▼) mouse are shown.

The results shown in FIG. 1-7, have been obtained with an ELISA test.

Figure 8:
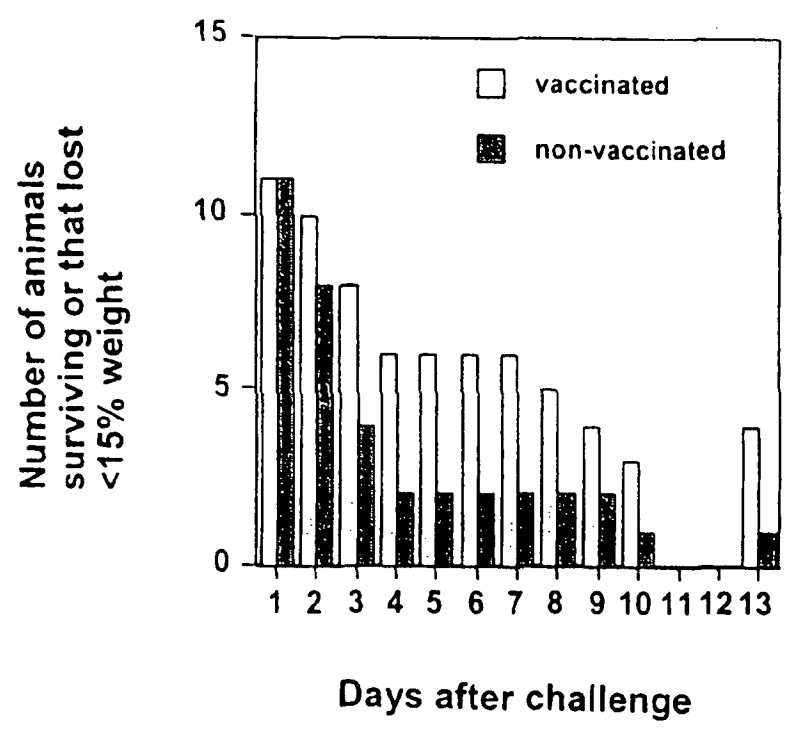

FIG. 8 shows the accumulated number of mice that survived or lost less than 15% of weight after subcutaneous immunization with FNZN, SFSC1, and EAG4B followed by challenge with *Streptococcus equi* subsp. *equi* (n=24).

Figure 9:
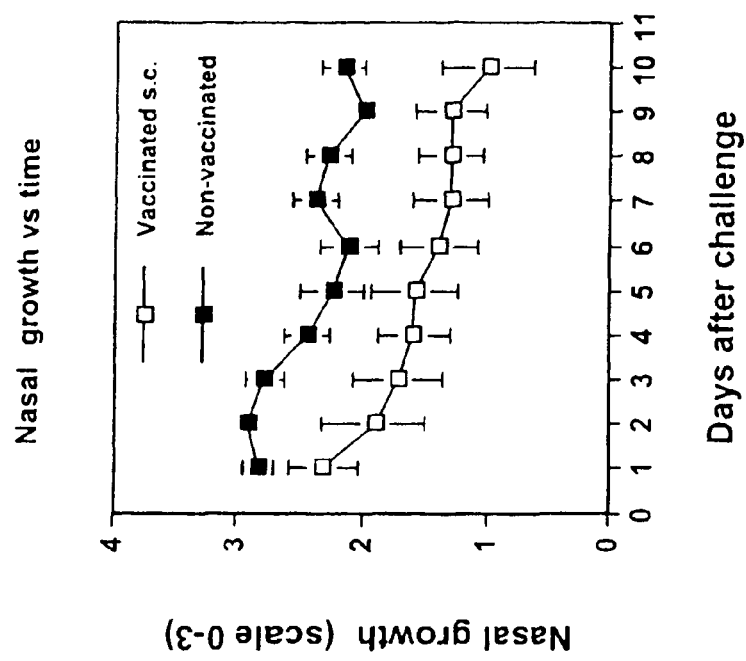

FIG. 9 shows nasal growth after subcutaneous immunization of mice with FNZN, SFSC1, and EAG4B followed by challenge with *Streptococcus equi* subsp. *equi*. Growth is determined on a scale of 0-3 (n=24). Mean and SE (Standard Error) are shown. The control group was not immunized.

Figure 10:
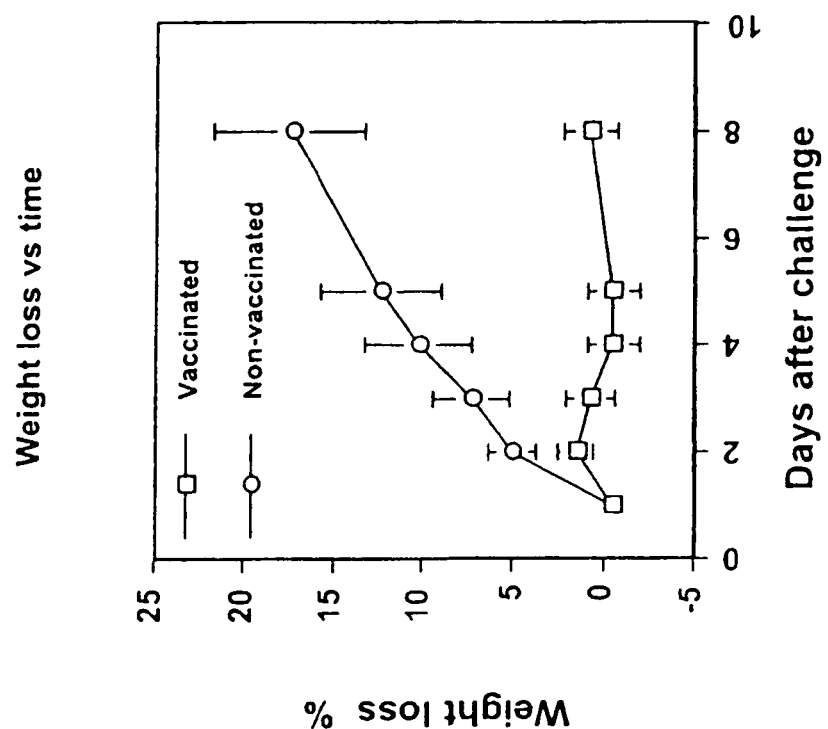

FIG. 10 shows weight loss of mice after intranasal immunization of mice with FNZN, SFSC1, and EAG4B followed by challenge with *Streptococcus equi* subsp. *equi* (n=24). The control group was not immunized.

Figure 11:
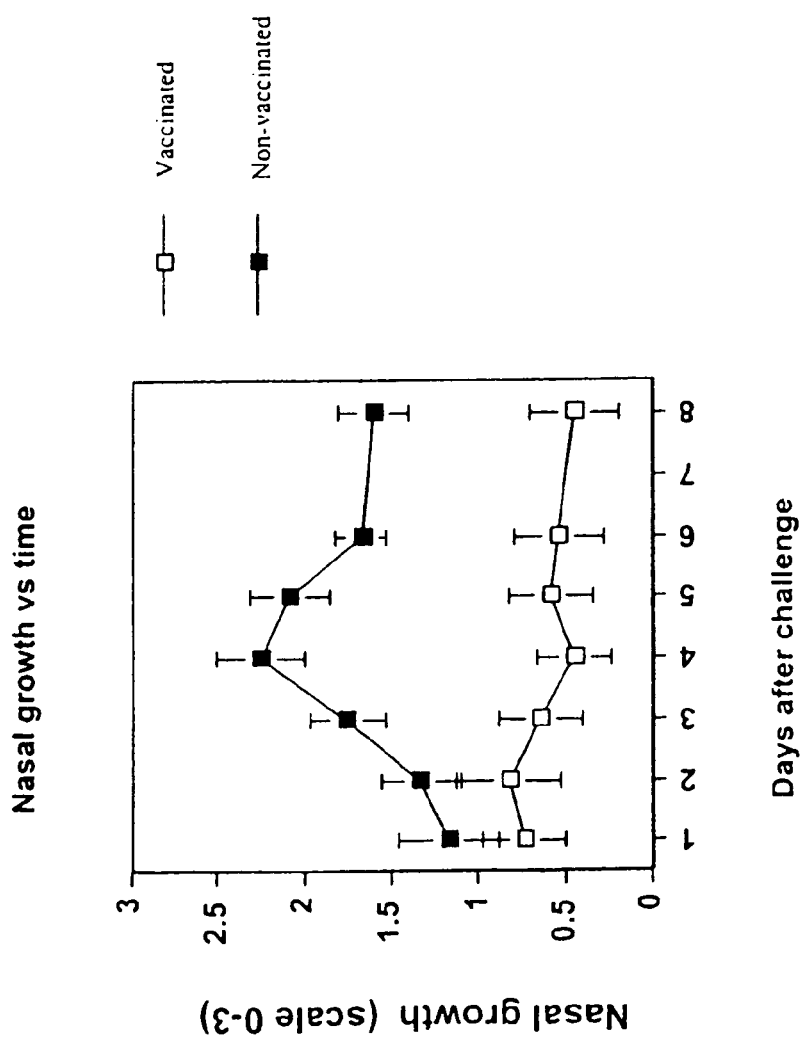

FIG. 11 shows nasal growth after intranasal immunization of mice with FNZN, SFSC1, and EAG4B followed by challenge with *Streptococcus equi* subsp. *equi* (n=24). Mean and SE are shown.

Figure 12:
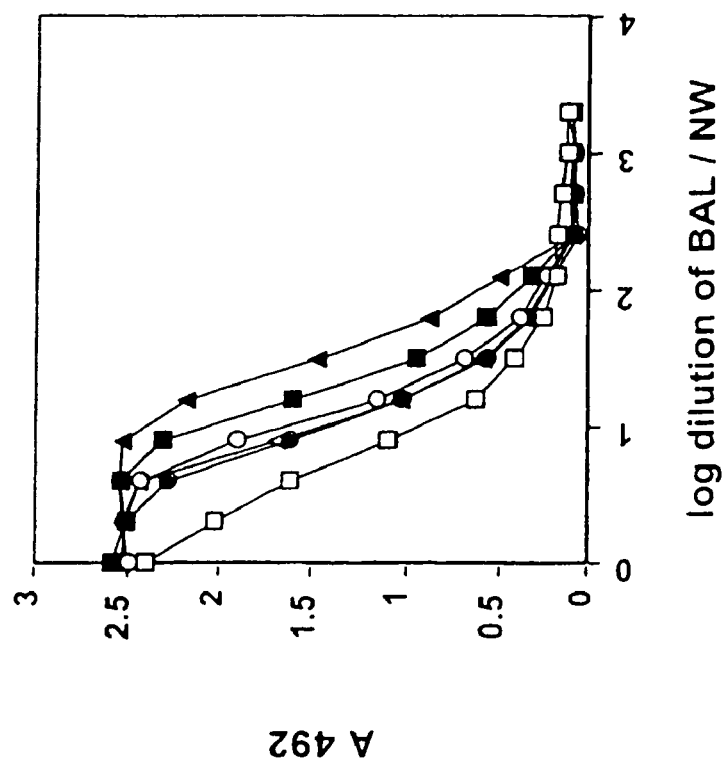

FIG. 12 shows IgA antibodies against SFSC1 in broncho-alveolar lavage (BAL) and nasal washes (NW) from mice nasally immunized with FNZN, SFSC1, and EAG4B. Results from six animals are shown.

Figure 13:
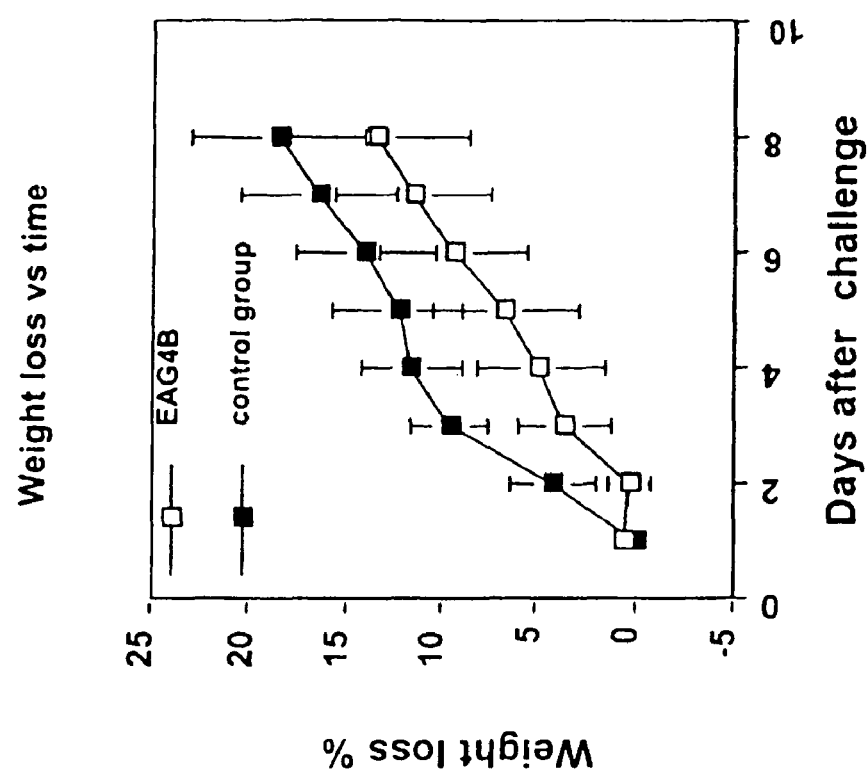

FIG. 13 shows weight loss of mice after intranasal immunization of mice with EAG4B followed by challenge with *Streptococcus equi* subsp. *equi* (n=10). The control group was not immunized.

Figure 14:
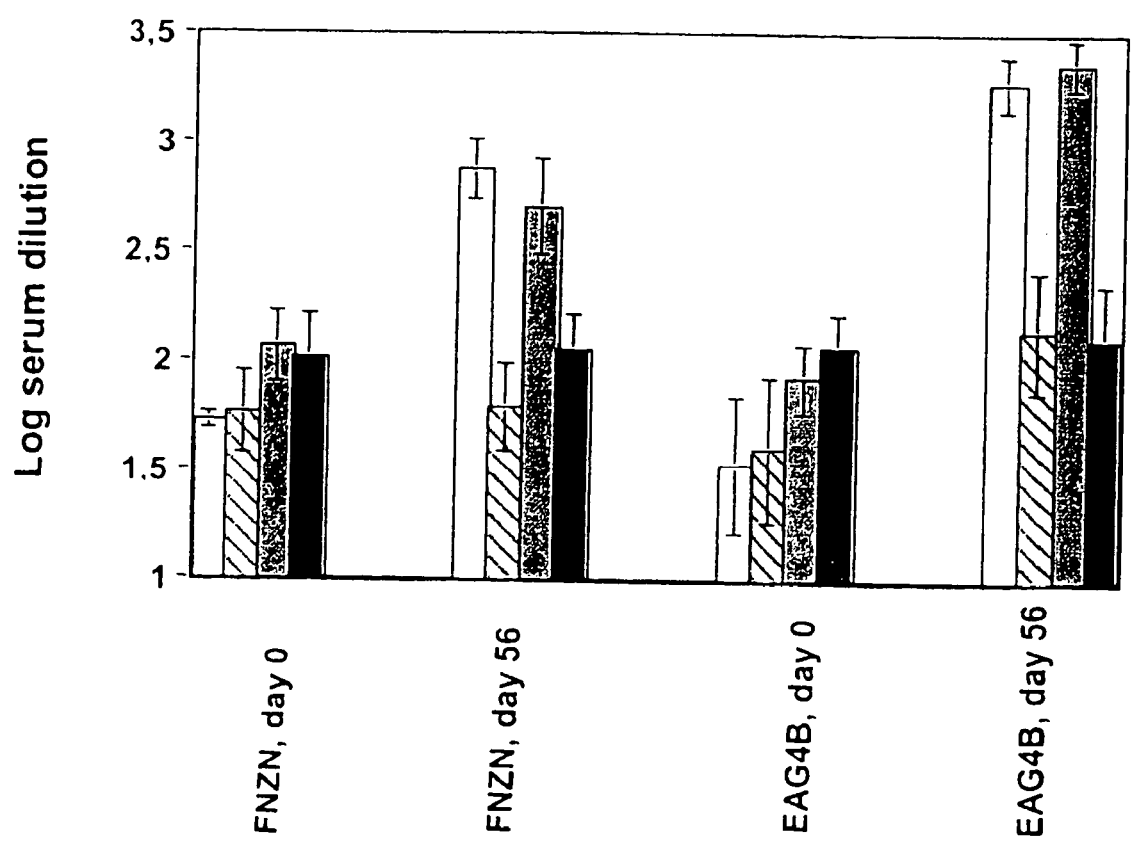

FIG. 14 shows IgG antibodies in immunized horses developed against EAG4B and FNZN.

Figure 15:
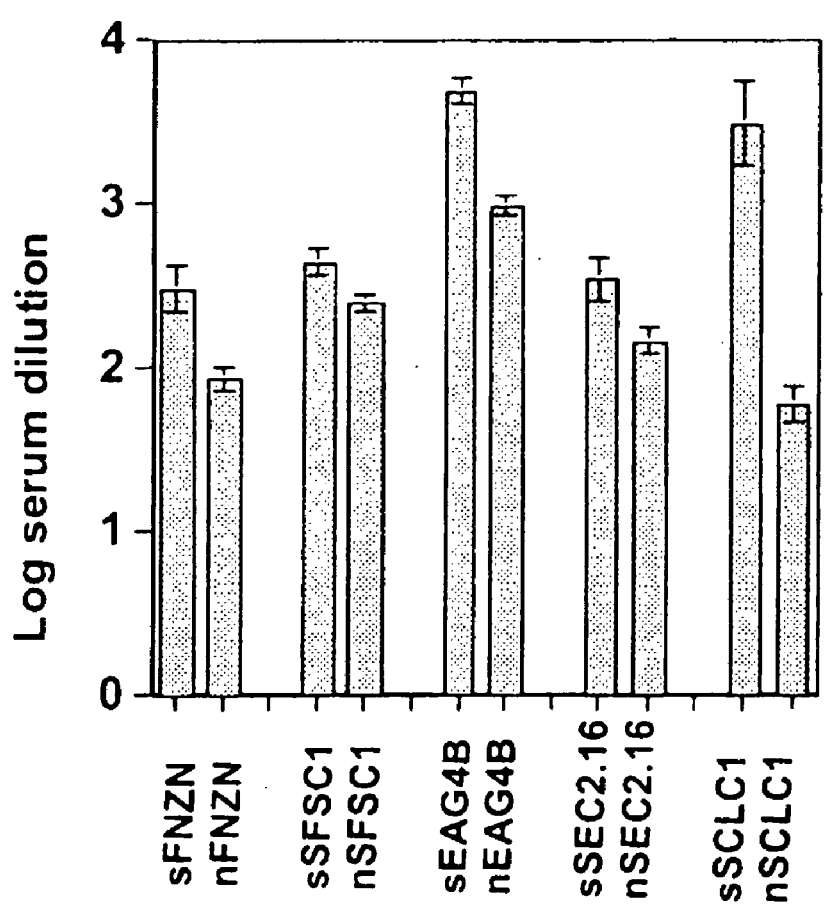

FIG. 15 shows the results from a comparison of serum antibody titers from horses with or without a history of strangles.

Figure 16:
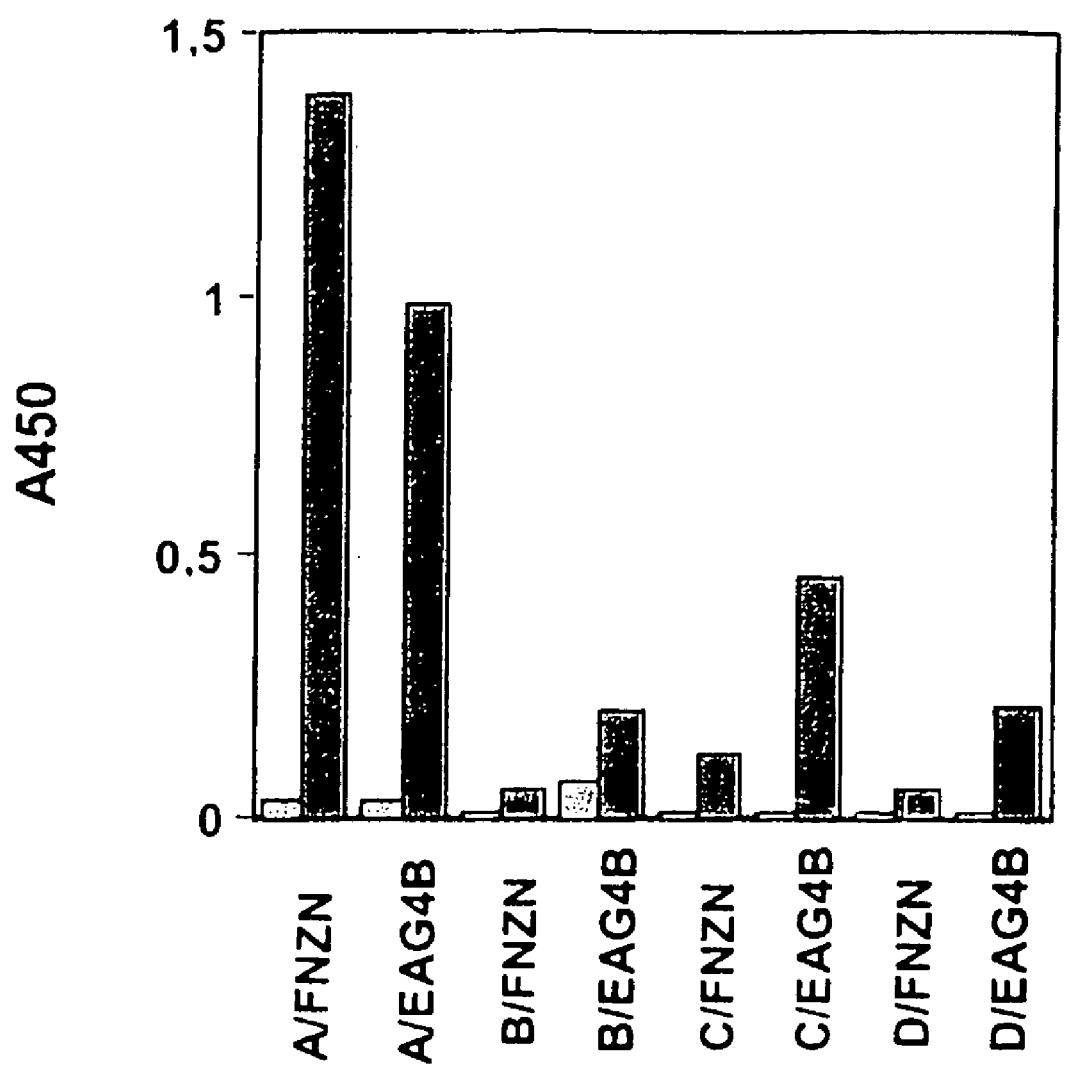

FIG. 16 shows the presence of IgA antibodies in nasal washings from immunized horses.

Figure 17:
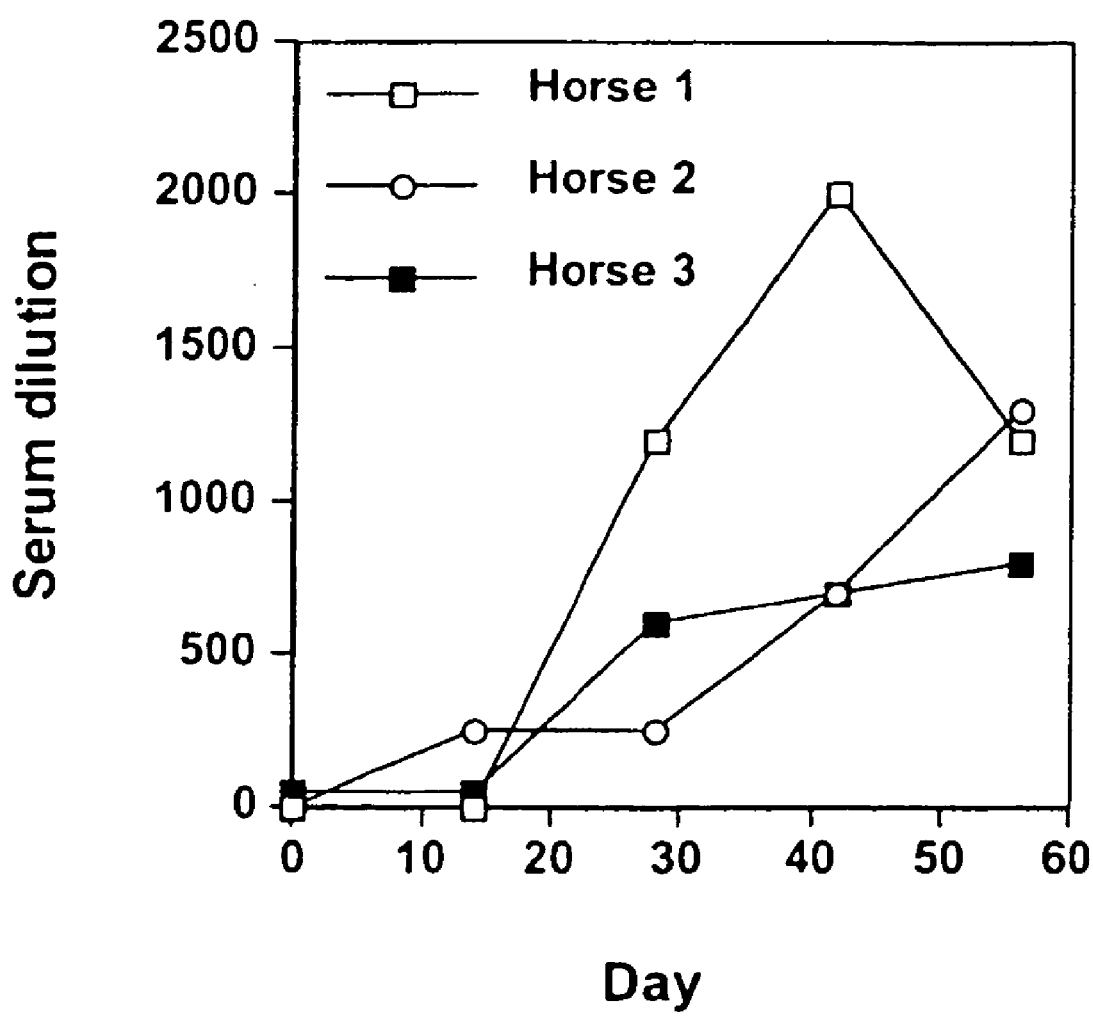
Figure 18:
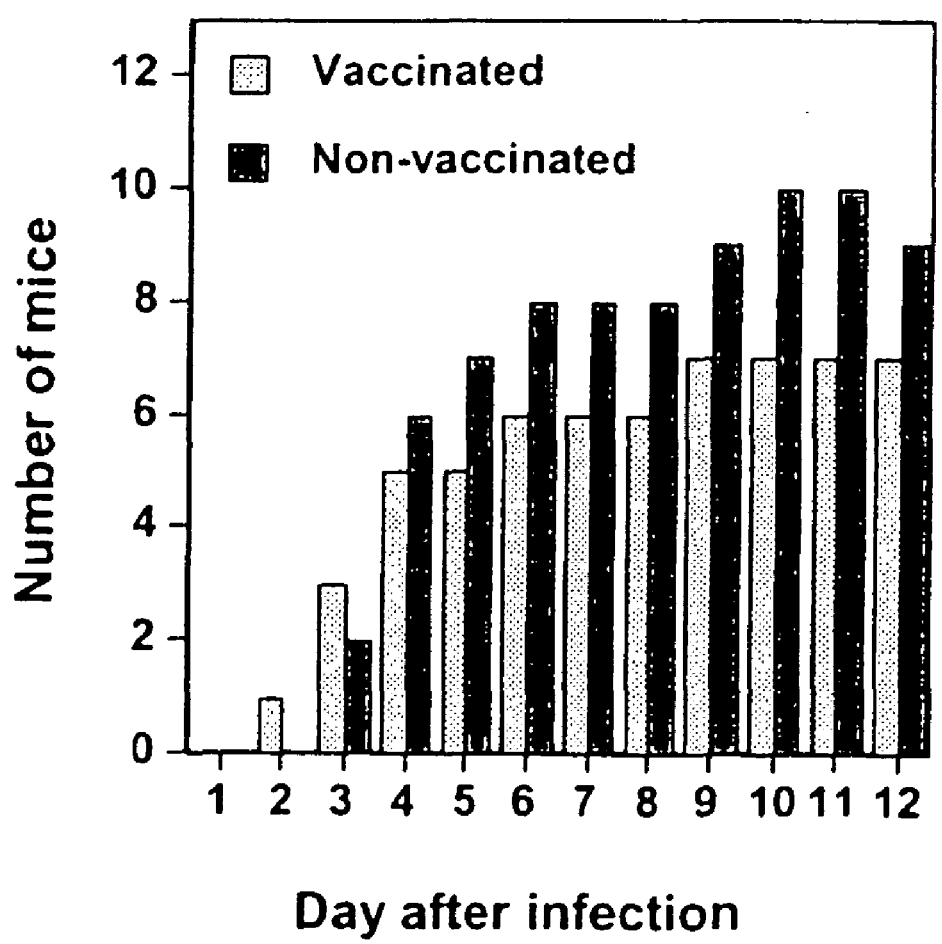

FIG. 17 shows antibody titers against EAG4B in horses immunized with EAG4B, FNZN, and SFSC1 as a function of time FIG. 18 shows the results obtained for mice (n=15) that were immunized with SEC2.16 using Matrix as adjuvant. The number of animals that lost more than 15% of weight or that died is shown as a function of time.

Figure 19:
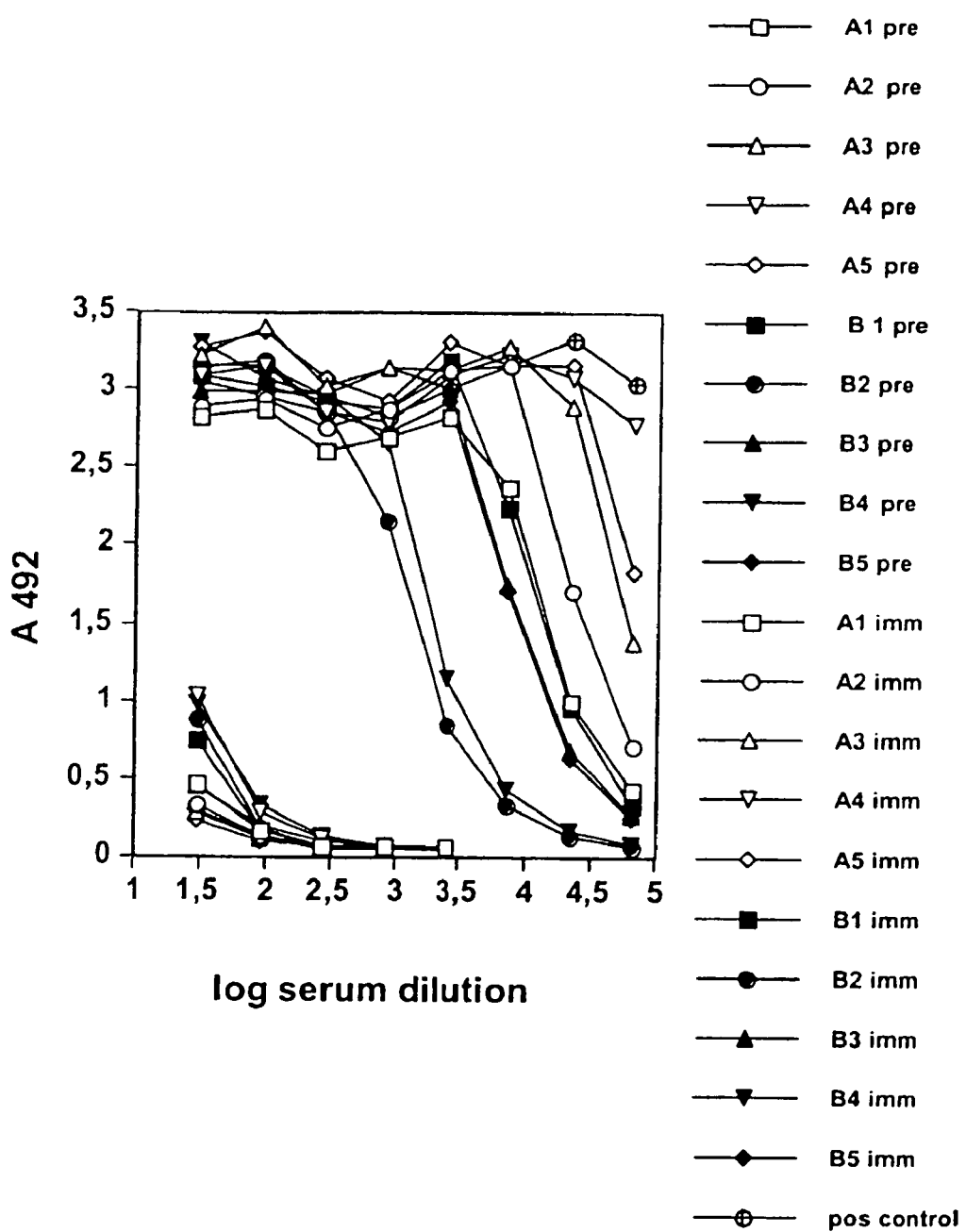

FIG. 19 shows the results obtained for mice that were immunized with SEC2.16 alone (group B (n=5)) or SEC2.16 together with Matrix (group A (n=5)). Serum samples were taken before (denoted pre) and after (denoted imm) immunization.

DETAILED DESCRIPTION OF THE INVENTION

The present invention is directed to an antigenic composition comprising at least one antigen, wherein said at least one antigen comprises at least part of a protein of *Streptococcus equi* subsp. *equi*, and said at least part of said protein comprises at least one antigenic epitope or antigenic determinant of *Streptococcus equi*, and wherein said protein is comprised of a protein that is designated EAG and comprises an N-terminal amino acid sequence, which is shown below as SEQ. ID. NO: 1 and is designated EAG4B.

```
SEQ. ID. NO: 1:
  1 MALDATTVLE PTTAFIREAV REINQLSDDY ADNQELQAVL ANAGVEALAA DTVDQAKAAL

61 DKAKAAVAGV QLDEARREAY RTINALSDQH KSDQKVQLAL VAAAAKVADA ASVDQVNAAI

121 NDAHTAIADI TGAALLEAKE AAINELKQYG ISDYYVTLIN KAKTVEGVNA LKAKILSALP
```

According to a suitable embodiment of the present invention, said antigenic composition comprises at least one further antigen that comprises at least part of a fibronectin-binding protein of *Streptococcus equi*, said at least part of said protein comprising at least one antigenic epitope or antigenic determinant of *Streptococcus equi*, and wherein said protein is selected from the group consisting of FNZ (EMBL sequence data bank accession number X99995) comprising an amino acid sequence as shown in SEQ. ID. NO: 2 below:

Suitably, the afore-mentioned antigenic compositions also comprise at least one further antigen that comprises at least part of an extracellular matrix-binding protein of *Streptococcus equi* and said at least part of said protein comprises an antigenic epitope or an antigenic determinant of *Streptococcus equi* and wherein said protein is comprised of a protein that is designated SEC and comprises an amino acid sequence as shown in SEQ. ID. NO: 4 below.

```
MKTKSFRKVLTTSATCIVLATSFAGGTLRVWAEQLYYGWNDGTRQSSPYFLYVSPKNAPKRE

LKDEYVVYCFNKKLYWPDQWESIYSNFNDIRSPYNDLPVYEKKLGYDGIFKQYAPDYKKDIS

DIASALVAVLSNGYPTNKSQLSTSYHLNNDSSRKVTQLAIWYFSDSLTKEYLKDTGGYNLND

MEKKALDFLISKGEDSKLKSEQSNYSLDIVYQSGGHDHMKDYQNLLGSTLIPKEPLKPQLG

GFSGHNGNGLSGLEGGSSGSQETNEDGKKGLIGFHGGLSGSEGKRDPLPGLKGEAGAPDTPQ

KPNDPLQGLEGGNSPIVEQNYGSTEGYHGQSGILEETEDTNPPGIILGGSGNVETHEDTRNP

HLMGIGGGLAGESGETTPKPGQTGGQGPVIETTEDTQKGMSGQSGGTIESENTKKPEVMIGG

QGQTIETTEDTQKGMSGQSGGTIESEDTKKPEVMIGGQGQIIDFSENTQSGMSGQSGDTTVI

EDTKKSEIIGGQGQIIDFSEDTQPGMSGQSGGTTIVEDTKKPTPKPKPAPAPIVNDEKPNK

GTHLPQTSDMKQLTLSIIGAMSMLLVLCLSLFKRPSKKD
``` and SFS comprising an amino acid sequence as shown in SEQ. ID. NO: 3 below:

```
MRKTEGRFRTWKSKKQWLFAGAVVTSLLLGAALVFGGLLGSLGG

SSHQARPKEQPVSSIGDDDKSHKSSSDSMVSRPPKKDNLQPKPSDQPTNHQHQATSPS

QPTAKSSGHHGNQPQSLSVNSQGNSSGQASEPQAIPNQGPSQPLGLRGGNSSGSGHHH

QPQGKPQHLDLGKDNSSPQPQPKPQGNSPKLPEKGLNGENQKEPEQGERGEAGPPLSG

LSGNNQGRPSLPGLNGENQKEPEQGERGEAGPPSTPNLEGNNRKNPLKGLDGENKPKE

DLDGKGLSGENDESPKLKDEHPYNHGRRDGYRVGYEDGYGGKKHKGDYPKRFDESSPK

EYNDYSQGYNDNYGNGYLDGLADRGGKRGYGYSYNPD.
```

SEQ. ID. NO: 4:
```
1                              27
LKQLTKIVSVVLLLVFTLSASLHXVRATNLSDNITSLTVASSSLRDGERTTVKVAFDD

KKQKIKAGDTIEVTWPTSGNVYIQGFNKTIPLNIRGVDVGTLEVTLDKAVFTFNQNIE

TMHDVSGWGEFDITVRNVTQTTAETSGTTTVKVGNRTATITVTKPEAGTGTSSFYYK

TGDMQPNDTERVRWFLLINNNKEWVANTVTVEDDIQGGQTLDMSSFDITVSGYRNE

RFVGENALTEFHTTFPNSVITATDNHISVRLDQYDASQNTVNIAYKTKITDFDQKEFA

NNSKIWYQILYKDQVSGQESNHQVANINANGGVDGSRYTSFTVKKIWNDKENQDGK

RPKTITVQLYANDQKVNDKTIELSDTNSWQASFGKLDKYDSQNQKITYSVKEVMVP

VGYQSQVEGDSGVGFTITNTYTPEVISITGQKTWDDRENQDGKRPKEITVRLLANDA

ATDKVATASEQTGWKYTFTNLPKYKDGKQITYTIQEDPVADYTTTIQGFDITNHHEV
```

-continued

```
ALTSLKVIKVWNDKDDYYHKRPKEITILLKADGKVIREHQMTPDQQGKWEYTFDQL

PVYQTGKKISYSIEEKQVAGYQAPVYEVDEGLKQVTVTNTLNPSYKLPDTGGQGVK

WYLLIGGGFIIVAILVLISLYQKHKRHNMSKP
                               657
```

The antigens of the present antigenic compositions may comprise the entire amino acid sequence of said protein or may comprise a fragment or analog thereof. Suitable fragments are N-terminal fragments of EAG and FNZ. An antigen derived from SFS may be comprised of a C-terminal part of SFS and an antigen derived from SEC may be comprised of a collagen-binding part of SEC.

A preferred antigenic composition of the present invention contains all the afore-said antigens EAG, FNZ, SFS, and SEC. Preferably, an N-terminal part of each of EAG and FNZ designated FNZN and EAG4B, respectively, a C-terminal part of SFS designated SFSC1 and a collagen-binding part of SEC designated SEC 2.16 are used in said composition.

From the above, it is evident that the present antigens that are derived from proteins of Streptococcus equi may comprise the entire protein, a fragment of said protein or an analog of said protein. Thus, the present invention is not limited to the fragments of proteins that are specifically disclosed herein.

A further embodiment of the present invention is concerned with a vaccine composition for protecting non-human mammals against infection of Streptococcus equi, which comprises an antigenic composition as disclosed above as immunizing component, and a pharmaceutically acceptable carrier.

Suitably, the present vaccine composition comprises an antigenic composition that contains all the afore-said antigens as immunizing component. Optionally, one or more of these antigens are comprised of analogs of said proteins or fragments thereof, e.g. N-terminal or C-terminal fragments.

The vaccine composition may comprise further components, such as an adjuvant. Suitably, said adjuvant stimulates systemic or mucosal immunity. Such adjuvants are well known in the art.

According to a suitable embodiment, the vaccine composition is a vaccine that protects susceptible mammals, suitably horses, against strangles caused by Streptococcus equi subsp. equi.

The vaccine composition of the present invention is provided in a physiologically administrable form. Suitably, it is administrable by subcutaneous or intranasal inoculation. Suitably, the vaccine composition of the present invention stimulates serum, mucosal and/or bronchial lavage antibody responses directed to Streptococcus equi antigens in mammals susceptible to Streptococcus equi, suitably horses.

The present invention is also related to a method for producing an antigen to be used in an antigenic composition of the present invention, which method comprises
  (a) providing a DNA fragment encoding said antigen and introducing said fragment into an expression vector;
  (b) introducing said vector, which contains said DNA fragment, into a compatible host cell;
  (c) culturing said host cell provided in step (b) under conditions required for expression of the product encoded by said DNA fragment; and
  (d) isolating the expressed product from the cultured host cell.

Preferably, said method further comprises a step (e) wherein the isolated product from step (d) is purified, e.g. by affinity chromatography or other chromatographic methods known in the art.

A further embodiment of the present invention is concerned with a method for preparation of a vaccine of the present invention, which vaccine contains as immunizing component an antigenic composition as disclosed above, said method comprising mixing said antigenic composition and a pharmaceutically acceptable carrier.

The present invention is also related to a method for the production of an antiserum, said method comprising administering an antigenic preparation of the present invention to an animal host to produce antibodies in said animal host and recovering antiserum containing said antibodies produced in said animal host.

Moreover, the present invention is concerned with a method of prophylactic or therapeutic treatment of S. equi infection in non-human mammals, suitably horses, comprising administering to said mammal an immunologically effective amount of a vaccine or an antiserum of the present invention.

A suitable embodiment of the present invention is concerned with a method for protecting horses against Streptococcus equi infection, which comprises inoculating a horse subcutaneously or intranasally or both subcutaneously and intranasally with a vaccine of the present invention to induce an immune response against Streptococcus equi in said horse. Suitably, an immune response in the form of IgG and IgA antibodies in the nasopharyngeal mucus is thereby induced in said horse.

The present invention describes the composition of a vaccine comprising one or several antigen components which have been prepared according to the present method using E. coli as host cells. The source of these antigens might also be the native bacteria, if methods are developed for expression and purification thereof. Alternatively, the antigens of the present invention can also be produced according to methods that are based on fusion strategies where various parts of the respective antigen are recombined resulting in a fusion protein consisting of parts from different antigens. This fusion strategy could also be suitable for introducing immune reactive part(s), e.g. T-cell epitopes or attenuated toxins (or parts thereof), thereby introducing other features suitable for optimizing the antigen presentation or localization.

EXPERIMENTAL PART

Example 1

Preparation of Antigens Derived from EAG

A gene similar to the afore-mentioned zag gene (the GeneBank accession number for the nucleotide sequence of zag is U2582) from S. equi subsp. zooepidemicus but present in subsp. equi has been described in Lindmark et al (1999) (Ref 11) and Lindmark (1999) (Ref. 13). This gene that is present in subsp. equi and encodes the afore-mentioned protein EAG is hereafter called eag. To clone and express a part of this gene encoding an N-terminal fragment (EAG4B) of EAG in *E. coli*, the following work was done.

Construction

The primers

```
OZAG43B:                                    (SEQ. ID. NO: 5)
5'-TTT TCT CGA GCT ACG GTA GAG CTG ATA AAA TCT C-3'
and OZAG15:                                     (SEQ. ID. NO: 6)
5'-TCA GCC ATG GCT CTA GAT GCT ACA ACG GTG TT-3'
``` were used to PCR-amplify a DNA-fragment corresponding to amino acid residues 34-262 in protein EAG using *S. equi* subspecies *equi* 1866 chromosomal DNA as a template. The PCR-product was digested with NcoI and XhoI and ligated into the pTYB4-vector obtained from New England Laboratories (NEB Inc) digested with the same enzymes. One µl of the ligation mixture was transformed into *E. coli* ER2566. Correct transformants were identified by colony screening using horse radish peroxidase-labeled human serum albumin. The clone chosen for further work was sequenced from both directions to verify the correct insertion into the vector and the presence of a stop codon between EAG and the intein-affinity tag.

HSA-Column 50 mg human serum albumin (HSA, Sigma) were immobilized on a 5 ml HITRAP™ NHS-activated column (Pharmacia Biotech) according to the manufacturer's instructions. Based on the absorbance at 280 nm, 65% of the HSA was estimated to be immobilized on the column.

Expression and Purification—General 16 ml of an over night culture of EAG4B in *E. coli* ER2566 were inoculated into 2 liters of LB-medium supplemented with 50 µg ampicillin per ml. The culture was incubated at 37° C. until an $OD_{600}$ in the range of 0.5-0.6 was reached. Thereafter, IPTG was added to a final concentration of 0.5 mM and the culture was incubated at 25° C. over night.

The culture was harvested and the pellet was washed once in 50 ml PBS-D before it was resuspended in 40 ml of 20 mM Na phosphate, pH 7.0 (binding buffer). The resuspension was divided into two tubes and 10 mg lysozyme were added to each tube. After 2 hrs. of incubation at 37° C., the tubes were frozen at −20° C. over night.

The lysate was sonicated to fragmentize the DNA, centrifuged and the supernatant was filtered through a 0.45 µm filter.

The column was washed with 30 ml binding buffer before the sample (corresponding to 1 liter of the over night culture) was applied onto the column. Thereafter, the column was washed with 50 ml binding buffer and the $A_{280}$ value was confirmed to be below 0.010. Bound protein was eluted in 0.1 M glycine-HCl, pH 3.0. The first 4.5 ml were not collected while the next 10 ml were collected as 1 ml fractions, which were neutralized by addition of 100 µl 1 M Tris-buffer, pH 8.0. Then, the column was regenerated by addition of binding buffer and stored at +4° C. in the presence of sodium azide.

The $A_{280}$ value was determined and the fractions containing protein, normally fractions 1 to 5 or 6 were pooled and dialyzed 3 times against 4 liters of PBS-D. Thereafter, the protein was concentrated by extracting water from the dialysis tubing with PEG 30 000.

From an over night culture of 2 liters, this procedure yielded 5-6 mg of an N-terminal fraction of the EAG protein, designated EAG4B and comprising the amino acid sequence recited above as SEQ. ID. NO: 1. In this sequence, the first amino acid presented in bold originates from the vector.

The nucleotide sequence of the fragment encoding EAG4B where the coding sequence starts from nucleotide 38(A) and ends at nucleotide 577(C) is shown below (SEQ. ID. NO: 7).

```
SEQ.ID. NO: 7:
                 10        20        30        40        50
                 |         |         |         |         |
   1 AAATAATTTTGTTTAACTTTAAGAAGGAGATATAACCATGGCTCTAGATG

51 CTACAACGGTGTTAGAGCCTACAACAGCCTTCATTAGAGAAGCTGTTAGG

101 GAAATCAATCAGCTGAGTGATGACTACGCTGACAATCAAGAGCTTCAGGC

151 TGTTCTTGCTAATGCTGGAGTTGAGGCACTTGCTGCAGATACTGTTGATC

201 AGGCTAAAGCAGCTCTTGACAAAGCAAAGGCAGCTGTTGCTGGTGTTCAG

251 CTTGATGAAGCAAGACGTGAGGCTTACAGAACAATCAATGCCTTAAGTGA

301 TCAGCACAAAAGCGATCAAAAGGTTCAGCTAGCTCTAGTTGCTGCAGCAG

351 CTAAGGTGGCAGATGCTGCTTCAGTTGATCAAGTGAATGCAGCCATTAAT

401 GATGCTCATACAGCTATTGCGGACATTACAGGAGCAGCCTTGTTGGAGGC

451 TAAAGAAGCTGCTATCAATGAACTAAAGCAGTATGGCATTAGTGATTACT

501 ATGTGACCTTAATCAACAAAGCCAAAACTGTTGAAGGTGTCAATGCGCTT

551 AAGGCAAAGATTTTATCAGCTCTACCGTAGCTCGAGCCCGGGTGCTTTGC
```

Example 2

Preparation of Antigens Derived from SFS

The SFS protein from *S. equi* subsp. *equi* has previously been described by Lindmark and Guss (1999) (Ref 12) and in WO 00/37496. The GeneBank accession number for the nucleotide sequence of the sfs gene is AF 136451.

A C-terminal fragment of this protein was produced as follows:

The 3' end of the sfs gene was PCR amplified using the Taq DNA polymerase (Amersham) and chromosomal DNA from *S. equi* strain 1866 as template and the synthetic oligonucleotides OSFS25: 5'-GGTCCCATGGCAACTCCGAATTTA-GAAGGA-3' (SEQ. ID. NO: 8) and OSFS23: 5'-CAGACTC-GAGGTCGGGATTGTAAGAATAG-3' (SEQ. ID. NO: 9) as primers. The PCR procedure was performed in 100 µl under standard conditions as regards buffer, template and primer concentration. The PCR cycles were performed under the following conditions: 1 min. of denaturation at 94° C., 30 sec. of annealing at 40° C., and 2 min. of extension at 72° C., which were repeated as 25 cycles. After amplification, the PCR product was purified using phenol extractions, chloroform extractions and EtOH precipitation. The purified DNA was cleaved with the restriction enzymes NcoI and XhoI after which the DNA was purified as described above.

The DNA obtained above was ligated into the plasmid vector pTYB4 [(New England Biolabs, Beverly, Mass., USA (NEB Inc.)], which previously had been digested with the same restriction enzymes and treated with alkaline phosphatase. After ligation (using the READYTOGO™ ligation kit, Amersham), the DNA sample was electrotransformed into the E. coli strain ER2566 and spread on LAA-plates (Luria Bertani agar plates supplemented with ampicillin, final conc. 50 µg/ml). After incubation over night at 37° C., clones harboring plasmids with inserts were isolated and the presence of the correct insert was verified by DNA sequencing. One of the clones thereby obtained, called SFSC 1, was chosen for production of the C-terminal part of SFS.

The vector used is a part of an E. coli expression and purification system called IMPACT$^T$ T7 (NEB Inc.). Briefly, following the manufacturer's instructions, the clone SFSC1 was grown at 37° C. in Luria Bertani growth medium supplemented with ampicillin (final conc. 50 µg/ml). At an optical density ($OD_{600}$) of ~0.6, the growth medium was supplemented with IPTG (final conc. 0.4 mM) and the growth temperature was shifted to 20° C. After incubation over night, the cells were harvested and resuspended in a buffer [20 mM Tris-HCl (pH 8.0), 500 mM NaCl, 0.1 mM EDTA, and 0.1% TRITON™ X100 (octylphenol ethylene oxide condensate), lysed by freezing and thawing, and after centrifugation, the supernatant was sterile filtered and applied to a chitin column.

The column was extensively washed using the same buffer as above and was subsequently treated with cleavage buffer [20 mM Tris-HCl (pH 8.0), 50 mM NaCl, 0.1 mM EDTA, and 30 mM dithiothreitol (DTT)]. The reducing conditions in the cleavage buffer induce an intein-mediated self-cleavage that releases the SFS part from the column while the intein-chitin-binding part remains bound. The eluted sample containing the product SFSC1 was dialysed against phosphate-buffered saline [PBS; 137 mM NaCl, 2.7 mM KCl, 10 mM $Na_2HPO_4$, 1.4 mM $KH_2PO_4$ (pH 7.4)] and concentrated. The amount of protein obtained was determined and the quality checked using SDS-PAGE.

After the intein part has been cleaved off from SFSC1, the purified protein has an amino acid sequence as recited below as SEQ. ID. NO: 10 except that the amino acid residues in bold are residues that correspond to the amino acid residues encoded by the pTYP4 vector, while remaining amino acid residues originate from the SFS protein.

Example 3

Preparation of Antigens Derived from FNZ

Protein FNZ from S. equi subsp. zooepidemicus has previously been described by Lindmark et al (1996) (Ref. 9), Lindmark (1999) (Ref. 13), Lindmark et al (1999) (Ref. 11) and Lindmark et al (2001) (Ref 14). The EMBL accession number for the nucleotide sequences of the fnz gene is X99995. A similar truncated protein called FNE is also expressed by strains of S. equi subsp. equi [Lindmark et al (2001), Ref. 14]. The GeneBank accession number for the nucleotide sequence of the fne gene is AF360373. The construction of a clone called pT2fnzN encoding the N-terminal part of FNZ has previously been described by Lindmark et al 2001 (Ref. 14). Briefly, the clone pT2fhzN was constructed as follows using PCR amplification with the forward primer OFNZ1:                              (SEQ. ID. NO: 11)
5'-ACCATGGCTAGCGCAGAGCAGCTTTATTATGGGT-3', and the reverse primer OFNZ2:                              (SEQ. ID. NO: 12)
5'-ATACCCGGGATATCCTTCGGTACTACCATAGT-3'.

Chromosomal DNA from subsp. zooepidemicus strain ZV was used as the template and the 5'end of the fnz gene was amplified. The PCR fragment obtained was cleaved with restriction endonucleases NheI and SmaI, followed by ligation into the corresponding restriction endonuclease sites in the expression vector pTYB2 (NEB). The ligated DNA was electrotransformed into E. coli strain ER2566. Plasmids harboring inserts were isolated from transformants and verified by DNA sequencing. One such clone is designated pT2fnzN. The production in E. coli and purification of the N-terminal part of FNZ, called FNZN, were performed as described above for protein SFSC1 and these steps are also described in Lindmark et al (2001) (Ref. 14).

The amino acid sequence of FNZN comprises then amino acid residues 32-337 of the amino acid sequence of the protein FNZ recited above as SEQ. ID. NO: 2. The corresponding amino acid sequence of FNZN is shown below as SEQ. ID. NO: 13.

```
SEQ. ID. NO: 13
M A S A E Q L Y Y G W N D G T R Q S S P

Y F L Y V S P K N A P K R E L K D E Y V

V Y C F N K K L Y W P D Q W E S I Y S N

F N D I R S P Y N D L P V Y E K K L G Y

D G I F K Q Y A P D Y K K D I S D I A S

A L V A V L S N G Y P T N K S Q L S T S
```

```
SEQ. ID. NO: 10:
MATPNLEGNN RKNPLKGLDG ENKPKEDLDG KGLSGENDES PKLKDEHPYN

HGRRDGYRVG YEDGYGGKKH KGDYPKRFDE SSPKEYNDYS QGYNDNYGNG

YLDGLADRGG KRGYGYSYNP DLEPG.
```

-continued

```
Y H L N N D S S R K V T Q L A I W Y F S

D S L T K E Y L K D T G G Y N L N D M E

K K A L D F L I S K G E D S K L K S E Q

S N Y S L D I Y V Y Q S G G H D H M K D

Y Q N L L G S T L I P K E P L K P Q L G

G P S G H N G N L S G L E G G S S G S

Q E T N E D G K K G L I G F H G G L S G

S E G K R D P L P G L K G E A G A P D T

P Q K P N D P L Q G L E G G N S P I V E

Q N Y G S T E G Y G
```

In the previously recited amino acid sequence (SEQ. ID. NO: 2) of protein FNZ, amino acids shown in bold originate from the protein FNZ in *S. equi* subspecies *zooepidemicus*, while those shown in normal type are derived from the expression vector construct. In SEQ. ID. NO: 13, the first three and the last amino acid residues originate from the vector.

Example 4

Preparation of Antigens Derived from the Protein SEC

The genome of *S. equi* is accessible (www.sanger.ac.uk) for computer analysis. By using earlier published sequences of virulence factors or potential virulence factors from pathogenic streptococci and staphylococci, it is possible to screen the genome of *S. equi* for the presence of similar genes. By using the soft ware program BLAST and searching for open reading frames encoding a protein similar to the collagen-binding protein CNA of *Staphylococcus aureus* (WO 92/07002), it was possible to identify a hypothetical gene of 1971 nucleotides in the *S. equi* genome encoding a protein of 657 amino acids. (Ref. 25, Lannergård et al. (2003)). This protein, hereafter termed protein SEC (SEQ. ID. NO: 4), encodes an N-terminal signal sequence (amino acid sequence 1-26) followed by a region, which displays collagen-binding. The C-terminal part of protein SEC contains all typical features of cell surface proteins from streptococci, like putative wall anchoring and membrane spanning regions, as well as a motif corresponding to the LPDTG motif (SEQ. ID). NO: 14) of the protein SEC.

The nucleotide sequence of the sec gene (later renamed to cne) encoding the protein SEC (the accession no. of the cne is AY193773). is shown below as SEQ. ID. NO: 15.

```
SEQ. ID. NO: 15:
1
TTGAAACAACTGACAAAGATCGTTAGTGTGGTCTTGTTGCTGGTCTTTACCGTTAG

TGCTAGCCTGCACAAGGTTCGGGCAACTAATCTTAGTGACAACATCACATCATTG

ACGGTTGCTTCTTCATCACTCCGAGATGGAGAGAGAACGACGGTAAAGGTTGCGT

TTGATGACAAAAAACAGAAAATCAAGGCAGGGGATACGATAGAGGTCACCTGGC

CTACAAGTGGTAATGTCTACATTCAGGGCTTTAATAAAACCATACCGCTTAATAT

TAGAGGGGTAGATGTTGGTACCTTGGAGGTCACGCTAGACAAGGCTGTTTTCACA

TTCAATCAAAATATTGAAACAATGCATGATGTCTCTGGTTGGGGAGAGTTTGATA

TTACTGTTAGAAATGTGACACAAACCACCGCTGAAACATCAGGAACGACCACAG

TAAAGGTAGGCAATCGCACTGCTACATCACTGTTACTAAGCCTGAGGCAGGCAC

TGGTACCAGCTCATTTTATTATAAGACTGGTGATATGCAGCCCAATGATACTGAG

CGTGTGAGATGGTTCCTGCTGATTAACAACAACAAGGAATGGGTGGCCAATACTG

TTACAGTCGAAGACGATATTCAAGGTGGTCAAACCTTGGATATGAGCAGCTTTGA

CATCACCGTATCTGGTTATCGTAACGAGCGCTTCGTTGGGGAAAACGCTCTGACA

GAGTTTCATACAACATTTCCAAATTCTGTCATTACGGCAACAGATAATCACATTA

GTGTGCGGTTAGATCAATATGATGCCTCACAAAACACTGTCAACATTGCTTATAA

GACAAAGATAACGGACTTTGACCAAAAAGAATTTGCCAACAACAGTAAAATCTG

GTACCAGATTTTATACAAGGATCAGGTATCGGGTCAAGAGTCAAACCACCAAGTA

GCCAATATCAATGCTAACGGCGGGGTTGATGGCAGTCGCTATACCAGCTTTACTG

TCAAGAAAATTTGGAATGACAAGGAAAATCAAGACGGTAAGCGTCCAAAGACTA

TTACTGTTCAGCTTTACGCCAATGATCAGAAAGTTAAGATAAGACCATTGAATT

GAGTGATACTAATAGCTGGCAAGCAAGTTTTGGTAAGCTGGATAAGTATGACAGT

CAGAACCAAAAAATTACCTACAGTGTCAAGGAATGTATGGTTCCTGTTGGCTACC

AATCGCAGGTTGAGGGGGATAGTGGAGTAGGATTTACCATTACCAACACCTATAC
```

```
ACCAGAGGTCATTAGCATTACCGGTCAAAAAACTTGGGACGACAGGGAAAACCA

AGACGGTAAACGTCCTAAGGAGATTACGGTTCGTTTATTGGCAAATGACGCTGCA

ACTGACAAGGTAGCAACTGCTTCAGAGCAAACCGGCTGGAAGTATACATTTACCA

ATCTACCGAAATACAAAGATGGTAAACAGATCACCTACACGATCCAAGAGGACC

CTGTGGCAGATTACACCACAACCATTCAGGGATTTGATATTACCAATCATCATGA

GGTAGCCTTGACCAGCCTAAAGGTCATCAAGGTTTGGAATGATAAGGACGATTAT

TACCATAAACGTCCCAAGGAGATTACCATTTTGCTAAAGGCAGATGGCAAGGTGA

TTCGTGAACATCAGATGACACCGGATCAGCAAGGAAAATGGGAATACACCTTTG

ACCAGCTGCCGGTCTATCAGACAGGCAAGAAAATCAGCTACAGCATTGAGGAAA

AACAGGTTGCTGGCTATCAAGCCCCTGTCTATGAGGTTGATGAAGGCTTGAAGCA

GGTCACTGTAACCAACACCCTTAACCCAAGCTACAAGCTGCCTGACACCGGAGGA

CAAGGAGTGAAATGGTACCTGTTAATCGGTGGCGGTTTTATCATCGTCGCAATCC

TTGTACTGATCAGCCTTTATCAAAAACACAAGCGCCATAACATGTCAAAACCA
                                                    1971
```

Construction of Recombinant Protein SEC Expressing Collagen-Binding Activity

To express and purify the collagen-binding activity of protein SEC, two different constructions were made. The first construct, encoding the major part of protein SEC was made as follows. The primers

```
                                        (SEQ. ID. NO: 16)
OSEC1:5:  5'-CATGCCATGGCAACTAATCTTAGTGACAACAT-3'
and
                                        (SEQ. ID. NO: 17)
OSEC3:3:  5'-CCGCTCGAGCTTGTAGCTTGGGTTAAGGGTGT-3'
``` were used to PCR-amplify a DNA-fragment corresponding to a sequence from amino acid no. 27 to amino acid no. 615 in protein SEC (SEQ. ID. NO: 4) using *S. equi* subspecies *equi* 1866 chromosomal DNA as a template.

The second construct encoding the N-terminal part of protein SEC was made as follows. The primers OSEC1:5 and

```
                                        (SEQ. ID. NO: 18)
OSEC2:3:  5'-CCGCTCGAGAAAGCTGGTATAGCGACTGCCAT-3'
``` were used to PCR-amplify a DNA-fragment corresponding to a sequence from amino acid no. 27 to amino acid no. 328 in protein SEC (SEQ. ID. NO: 4) using *S. equi* subspecies *equi* 1866 chromosomal DNA as a template.

Both PCR amplifications were performed using READY-TOGO™ PCR beads (Amersham Pharmacia Biotech Inc) and the PCR apparatus MINICYCLER™ (MJ Research, Inc, MA, USA) using a program comprising: step 1: 95° C., 1 min; step 2: 95° C., 30 sec.; step 3: 46° C., 15 sec.; and step 4: 72° C., 2 min; repeated as 25 cycles from step 2 to step 4. After PCR amplification, the respective PCR-products were purified and digested with restriction endonucleases NcoI and XhoI and ligated into the pTYB4-vector (NEB) digested previously with the same enzymes. One µl of the respective ligation mixture was transformed into *E. coli* ER2566. After IPTG induction, *E. coli* clones expressing collagen-binding were identified by colony screening using $^{125}$I-labeled collagen (collagen S, type I obtained from Boeringher Mannheim). Several clones of both types of constructions expressing collagen-binding were identified and further characterized. One of these clones called pSEC 2.16 harboring the PCR-fragment and originating from the PCR using OSEC 1:5 and 3:3 was chosen after DNA sequencing of the insert for production of a recombinant collagen-binding protein called protein SEC 2.16 and comprising amino acid residues 27-616 of SEQ. ID. NO: 4. The nucleotide sequence of this insert encoding the recombinant collagen-binding protein SEC2.16 is shown below as SEQ. ID. NO: 19. The nucleotides shown in bold represent nucleotides originating from the vector.

```
SEQ. ID. NO: 19: Insert of pSEC2.16
ATGGCAACTAATCTTAGTGACAACATCACATCATTGACGGTTGCTTCTTCATCACTCCGAGATGGA

GAGAGAACGACGGTAAAGGTTGCGTTTGATGACAAAAAACAGAAAATCAAGGCAGGGGATACGA

TAGAGGTCACCTGGCCTACAAGTGGTAATGTCTACATTCAGGGCTTTAATAAAACCATAGGGCTTA

ATATTAGAGGGGTAGATGTTGGTACCTTGGAGGTCACGCTAGACAAGGCTGTTTTCACATTCAAT

CAAAATATTGAAACAATGCATGATGTCTCTGGTTGGGGAGAGTTTGATATTACTGTTAGAAATGTG

ACACAAACCACCGCTGAAACATCAGGAACGACCACAGTAAAGGTAGGCAATCGCACTGCTACTAT
```

```
-continued
CACTGTTACTAAGCCTGAGGCAGGCACTGGTACCAGCTCATTTTATTATAAGACTGGTGATATTCA

GCCCAATGATACTGAGCGTGTGAGATGGTTCCTGCTGATTAACAACAACAAGGAATGGGTGGCC

AATACTGTTACAGTCGAAGACGATATTCAAGGTGGTCAAACCTTGGATATGAGCAGCTTTGACATC

ACCGTATCTGGTTATCGTAACGAGCGCTTCGTTGGGGAAAACGCTCTGACAGAGTTTCATACAAC

ATTTCCAAATTCTGTCATTACGGCAACAGATAATCACATTAGTGTGCGGTTAGATCAATATGATGC

CTCACAAAACACTGTCAACATTGCTTATAAGACAAAGATAACGGACTTTGACCAAAAAGAATTTGC

CAACAACAGTAAAATCTGGTACCAGATTTTATACAAGGATCAGGTATCGGGTCAAGAGTCAAACC

ACCAAGTAGCCAATATCAATGCTAACGGCGGGGTTGATGGCAGTCGCTATACCAGCTTTACTGTC

AAGAAAATTTGGAATGACAAGGAAAATCAAGACGGTAAGCGTCCAAAGACTATTACTGTTCAGCTT

TACGCCAATGATCAGAAAGTTAATGATAAGACCATTGAATTGAGTGATACTAATAGCTGGCAAGCA

AGTTTTGGTAAGCTGGATAAGTATGACAGTCAGAACCAAAAAATTACCTACAGTGTCAAGGAAGT

GATGGTTCCTGTTGGCTACCAATCGCAGGTTGAGGGGATAGTGGAGTAGGATTTACCATTACCA

ACACCTATACACCAGAGGTCATTAGCATTACCGGTCAAAAAACTTGGGACGACAGGGAAAACCAA

GACGGTAAACGTCCTAAGGAGATTACGGTTCGTTTATTGGCAAATGACGCTGCAACTGACAAGGT

AGCAACTGCTTCAGAGCAAACCGGCTGGAAGTATACATTTACCAATCTACCGAAATACAAAGATG

GTAAACAGATCACCTACACGATCCAAGAGGACCCTGTGGCAGATTACACCACAACCATTCAGGGA

TTTGATATTACCAATCATCATGAGGTAGCCTTGAGCAGCCTAAAGGTCATCAAGGTTTGGAATGAT

AAGGACGATTATTACCATAAACGTCCCAAGGAGATTACCATTTTGCTAAAGGCAGATGGCAAGGTG

ATTCGTGAACATCAGATGACACCGGATCAGCAAGGAAAATGGGAATACACCTTTGACCAGCTGC

CGGTCTATCAGGCAGGCAAGAAAATCAGCTACAGCATTGAGGAAAAACAGGTTGCTGGCTATCAA

GCCCCTGTCTATGAGGTTGATGAAGGCTTGAAGCAGGTCACTGTAACCAACACCCTTAACCCAAG

CTACAAGCTCGAGCCCGGG
```

The amino acid sequence of the recombinant collagen-binding protein SEC2.16 encoded by the insert of pSEC2.16 is shown below as SEQ. ID. NO: 20. The amino acids shown in bold represent amino acids originating from the vector.

the insert of pSEC 1.18, this clone was used for production of a recombinant collagen-binding protein called protein SEC 1.18. This protein SEC 1.18 comprises the amino acid sequence shown below as SEQ. ID. NO. 22. The

```
SEQ. ID. NO: 20: Protein SEC2.16
MATNLSDNITSLTVASSSLRDGERTTVKVAFDDKKQKIKAGDTIEVTWPTSGNVYIQGFNKTIPLNIRGV

DVGTLEVTLDKAVFTFNQNIETMHDVSGWGEFDITVRNVTQTTAETSGTTTVKVGNRTATITVTKPEA

GTGTSSFYYKTGDIQPNDTERVRWFLLINNNKEWVANTVTVEDDIQGGQTLDMSSFDITVSGYRNER

FVGENALTEFHTTFPNSVITATDNHISVRLDQYDASQNTVNIAYKTKITDFDQKEFANNSKIWYQILYKD

QVSGQESNHQVANINANGGVDGSRYTSFTVKKIWNDKENQDGKRPKTITVQLYANDQKVNDKTIELS

DTNSWQASFGKLDKYDSQNQKITYSVKEVMVPVGYQSQVEGDSGVGFTITNTYTPEVISITGQKTWD

DRENQDGKRPKEITVRLLANDAATDKVATASEQTGWKYTFTNLPKYKDGKQITYTIQEDPVADYTTTIQ

GFDITNHHEVALTSLKVIKVWNDKDDYYHKRPKEITILLKADGKVIREHQMTPDQQGKWEYTFDQLP

VYQAGKKISYSIEEKQVAGYQAPVYEVDEGLKQVTVTNTLNPSYKLEPG
```

The other clone obtained above that was chosen for further studies was called pSEC 1.18 and harbored the PCR-fragment originating from the PCR using OSEC 1:5 (SEQ. ID. NO. 16) and 2:3 (SEQ. ID. NO. 18). After DNA sequencing of corresponding nucleotide sequence is shown below as SEQ. ID. NO. 21. In this nucleotide sequence, the nucleotides shown in bold represent nucleotides originating from the vector.

SEQ. ID. NO. 21: Insert of pSEC1.18
ATGGCAACTAATCTTAGTGAGAACATCACATCATTGACGGTTGCTTCTTCATCACTCCGAGATGGA

GAGAGAACGACGGTAAAGGTTGCGTTTGATGACAAAAAACAGAAAATCAAGGCAGGGGATACGA

TAGAGGTCACCTGGCCTACAAGTGGTAATGTCTACATTCAGGGCTTTAATAAAACGATACCGCTTA

ATATTAGAGGGGTAGATGTTGGTACCTTGGAGGTCACGCTAGACAAGGCTGTTTTCACATTCAAT

CAAAATATTGAAACAATGCATGATGTCTCTGGTTGGGGAGAGTTTGATATTACTGTTAGAAATGTG

ACACAAACCACCGCTGAAACATCAGGAACGACCACAGTAAAGGTAGGCAATCGCACTGCTACTAT

CACTGTTACTAAGCCTGAGGCAGGCACTGGTACCAGCTCATTTTATTATAAGACTGGTGATATGC

AGCCCAATGATACTGAGCGTGTGAGATGGTTCCTGCTGATTAACAACAACAAGGAATGGGTGGC

CAATACTGTTACAGTCGAAGACGATATTCAAGGTGGTCAAACCTTGGATATGAGCAGCTTTGACAT

CACCGTATCTGGTTATCGTAACGAGCGCTTCGTTGGGGAAAACGCTCTGACAGAGTTTCATACAA

CATTTCCAAATTCTGTCATTACGGCAACAGATAATCACATTAGTGTGCGGTTAGATCAATATGATG

CCTCACAAAACACTGTCAACATTGCTTATAAGACAAAGATAACGGACTTTGAGCAAAAAGAATTTG

CCAACAACAGTAAAATCTGGTACCAGATTTTATACAAGGATCAGGTATCGGGTCAAGAGTCAAAC

CACCAAGTAGCCAATATCAATGCTAACGGCGGGGTTGATGGCAGTCGCTATACCAGCTTTCTCGA

GCCCGGG

The amino acid sequence of the recombinant collagen-binding protein SEC1.18 encoded by the insert of pSEC1.18 is shown below as SEQ. ID. NO: 22. The amino acids shown in bold represent amino acids originating from the vector.

omitted), the membrane was transferred to a solution of PBS-T containing $^{125}$I-labeled collagen. After 4 hrs. of incubation at RT under gentle agitation, the membrane was extensively washed using PBS-T (casein omitted) and subjected to SEQ. ID. NO: 22: Protein SEC 1.18.
MATNLSDNITSLTVASSSLRDGERTTVKVAFDDKKQKIKAGDTIEVTWPTSGNVYIQGFNKTIPLNIRGV

DVGTLEVTLDKAVFTFNQNIETMHDVSGWGEFDITVRNVTQTTAETSGTTTVKVGNRTATITVTKPEA

GTGTSSFYYKTGDMQPNDTERVRWFLLINNNKEWVANTVTVEDDIQGGQTLDMSSFDITVSGYRNER

FVGENALTEFHTTFPNSVITATDNHISVRLDQYDASQNTVNIAYKTKITDFDQKEFANNSKIWYQILYKD

QVSGQESNHQVANINANGGVDGSRYTSFLEPG

Production of Protein SEC 1.18 and Protein SEC 2.16

Since the vector used to construct the pSEC1.18 and pSEC 2.16 is a part of the IMPACT-system (NEB), the expression and purification of protein SEC1.18 and protein SEC2.16 were performed as described for protein SFSC1 and protein FNZN. After purification, protein SEC 1.18 and protein SEC 2.16 were analysed by SDS-PAGE using the PHASTSYSTEM™ (Amersham Pharmacia) and 8-25% g cocci. Use of the soft ware program BLAST resulted in the identification in *S. equi* of additional genes encoding potential virulence factors similar to *Streptococcus pyogenes*: C5a peptidase (gi:14195215, sp, P58099,SCA2 STRPY), SClB (emb: CAC33776.1), collagen-like protein similar to (ref: NP358996.1), speK (ref: NP 438166.1), exotoxin I (gi: 16923748, gb:AAL31571.1, AF438524.1), streptodomase (emb:CAA59264.1), a DNA entry nuclease (ref: NP 346391.1), trypsin resistant surface T6 protein (sp:P18481, TEE6 STRPY), M and M-like proteins, other fibronectin-binding proteins and other.

Furthermore, the computer analyses revealed several hypothetical proteins displaying a structure which is found in cell wall-associated proteins in Gram-positive cocci (Schneewind et al 1995, Ref. 15). At the N-terminal end of these proteins, a signal sequence is found and at the C-terminal end, a motif LPXTG (SEQ ID NO: 28) corresponding to the LPDTG motif (SEQ. ID. NO: 14) of the SEC protein is present, which is followed by a stretch of hydrophobic amino acids ending with a few charged amino acids constituting the membrane-spanning region. These proteins should also be considered as potential targets to be included in an efficient vaccine against *S. equi* infections.

-continued

```
L T A R L G G I D K K V E E A A Q K P G I P G P T
G P Q G P K G D K G D P G

A P G E R G P A G P K G D T G E A G P R G E Q G P
A G Q A G E R G P K G D

P G A P G P K G E K G D T G A V G P K G E K G D T
G A T G P K G D K G E R

G E K G E Q G Q R G E K G E Q G Q R G E K G E Q K
P K G D Q G K D T K P

S A P K A P E K A P A P K A P K A S E Q S S N P K
A P A P K S A P S K S A A

P T G Q K A A L P A T G E I N H P F F T L A A L S
V I A S V G V L T L K G K

K D
 302
```

The nucleotide sequence of the gene sclC encoding protein SclC is shown below as SEQ. ID. NO: 24.

```
SEQ. ID. NO: 24:
1
atgacaaacaaaacaaagcgtacaggattggtacgcaagtacggtgcctgctcagcagctatcgccttagcagctcttgcaagcctgg gagcaggtaaagcagtaaaggcagaccagccagcagcactaaaatatccagaacctagagactattttcttcatactcgtgaaggtgat gttatttatgatgaggatataaaaagatattttgaggatttagaagcctatttaacagctagacttggtgggattgataaaaaagtagaagaa gctgcccaaaagccaggtattccaggtcctactggccctcaaggtcctaagggagacaaaggagatccaggtgcccctggtgagcgc ggtccagctggaccaaagggcgatacgggcgaagccggaccaagaggtgagcaaggcccagccggacaagctggagaacgtgg accaaaaggagatccaggtgctccaggtcctaaaggtgaaaagggtgatactggtgcagttggtcctaaaggtgaaaaaggtgatacc ggagcaaccggaccaaagggagacaagggcgaacgcggtgaaaaaggcgagcaaggccaacgtggcgaaaaaggcgagcaa ggccaacgcggtgaaaaaggcgagcaaaaaccaaagggtgatcaaggaaaagatacaaaaccatcagctccaaaagcacctgaaa aggctcctgcaccaaaagctccaaaggcttcagagcagtcatctaatcctaaagcaccagctcctaagtcagcaccaagcaaatcagc ggcaccaacaggtcaaaaagcagccctaccagcaacaggggaaatcaaccacccattcttcacccttgcagctcttagtgtcatcgcta gcgtaggcgtcctaactctaaaaggaaaaaaagactaa
                                            909
```

Based on considerations as discussed above, two proteins have been prepared and evaluated as disclosed in the following Examples 5 and 6.

Example 5

Preparation of Protein ScLC and Protein SCLC1

The amino acid sequence of *Streptpcoccus pyogeties* protein SclB was used to screen the genome of *S. equi* (www.sanger.ac.uk) using the software program BLAST. As a result of this screening, an open reading frame was identified, which encodes a protein called SclC, which is similar to SclB. The protein SclC comprises an amino acid sequence as shown as SEQ. ID. NO: 23 below.

```
SEQ. ID. NO: 23:
1
M T N K T K R T G L V R K Y G A C S A A I A L A A
L A S L G A G K A V K A D

Q P A A L K Y P E P R D Y F L H T R E G D V I Y D
E D I K R Y F E D L E A Y
```

To express and purify the major part of the SclC protein, the following construction was made. The primers

```
                                        (SEQ. ID. NO: 25)
OSCL2:5:  5'-CATGCCATGGACCAGCCAGCAGCACTAAAATAT-3'
and (SEQ. ID. NO: 26)
OSCL3:3:  5'-CCGCTCGAGGGCTGCTTTTTGACCTGTTGGT-3'
``` were used to PCR-amplify a DNA-fragment corresponding to amino acid 38 to amino acid 269 in protein SclC using *S. equi* subspecies *equi* 1866 chromosomal DNA as a template. PCR amplification was performed using READYTOGO™ PCR beads (Amersham Pharmacia Biotech Inc) and the PCR apparatus MINICYCLER™ (MJ Research, Inc, MA, USA) using a program of step 1: 95° C., 1 min; step 2: 95° C. 30 sec.; step 3: 50° C. 15 sec.; step 4: 72° C., 1 min; repeated as 24 cycles from step 2 to step 4. After PCR amplification, the respective PCR-products were purified and digested with restriction endonucleases NcoI and XhoI and ligated into the pTYB4-vector (NEB) previously digested with the same enzymes.

One μl of the respective ligation mixture was transformed into E. coli ER2566. E. coli clones harboring the sc/c fragment were identified by DNA sequencing of the inserted fragments.

Of these clones, one clone called pSclC1 and harboring the PCR-fragment originating from the PCR using OSCL2:5 (SEQ. ID. NO: 25) and OSCL3:3 (SEQ. ID. NO: 26), was chosen for production of a recombinant SclC protein called protein SCLC1. This protein SCLC1 comprises the amino acid sequence shown below as SEQ. ID. NO: 27.

```
SEQ. ID. NO: 27:
M D Q P A A L K Y P E P R D Y F L H T R E G D V I
Y D E D I K R Y F E D L E

A Y L T A R L G G I D K K V E E A A Q K P G I P G
P T G P Q G P K G D K G D

P G A P G E R G P A G P K G D T G E A G P R G E Q
G P A G Q A G E R G P K

G D P G A P G P K G E K G D T G A V G P K G E K G
D T G A T G P K G D K G

E R G E K G E Q G Q R G E K G E Q G Q R G E K G E
Q K P K G D Q G K D T

K P S A P K A P E K A P A P K A P K A S E Q S S N
P K A P A P K S A P S K S

A A P T G Q K A A L E P G
```

In the peptide sequence of the insert of pSclC1 encoding the recombinant protein SCLC1 (SEQ. ID. NO: 27), the amino acids shown in bold represent amino acids originating from the vector.

Production of Protein SCLC1

Since the vector used to construct the pSclC1 is a part of the IMPACT-system (NEB) the expression and purification of protein SCLC1 was performed as described for the other IMPACT-constructions (proteins SFSC1, FNZN, SEC 1.18 and SEC 2.16). After purification protein SCLC1 was analysed by SDS-PAGE using the PHASTSYSTEM™ (Amersham Pharmacia) and 8-25% gradient gels under reducing conditions (SDS buffer strips, boiling the samples in a sample buffer containing SDS and beta-mercaptoethanol before applying the samples on the gels). The results showed that the purified protein had a relative molecular weight corresponding to its calculated molecular weight. The purified protein SCLC1 was then used to immunize mice and rabbits and was also used to screen convalescence sera from horses for measurements of antibody titers against SCLC1. This is illustrated in Example 6 below.

Example 6

Immunization of Rabbits using Protein SCLC1 and Western Blot

Protein SCLC1 was used to immunize a rabbit. This work was done at the company Agrisera (Vännäs, Sweden). Using an ELISA format, where the SCLC1 protein was immobilized in microtiter wells, the immune serum obtained was analysed for presence of antibodies against SCLC1. The results showed that the immune sera could be diluted >30 000 and still react with the SCLC1 protein (as compared to the pre-immune serum, which did not contain any significant level of antibodies against SCLC1).

In a Western blot analysis, the SCLC1 protein was also run on an SDS-PAGE gel using the PHASTSYSTEM™ (Amersham Pharmacia) and 8-25% gradient gel under reducing conditions. After the electrophoresis had been completed, the SCLC1 protein was diffusion blotted to a nitrocellulose-membrane. After blocking, the membrane was divided and immune serum (dilution 1:10 000 in PBS-0.05% 20TWEEN™ 20 (polyoxyethylene sorbitan monolaurate)) and pre-immune serum, respectively, were added and incubated for two hours at room temp. After washing in PBS-0.05% TWEEN™ 20 (polyoxyethylene sorbitan monolaurate), secondary antibodies (anti rabbit IgG, horseradish-labelled and developed in goat, Sigma) were used to detect rabbit antibodies directed against SCLC1. The result showed that the immune serum detected the immobilized SCLC1 protein efficiently, while no detection was seen using the pre-immune serum.

Occurrence of sclC Gene in Strains of subsp. *equi* and subsp. *zooepidemicus*

Chromosomal DNA from different isolates of both subsp. *was* used as template for a PCR-analysis to study the occurrence of the sclC gene. The PCR primers used were OSCL2:5 (SEQ. ID. NO: 25) and OSCL3:3 (SEQ. ID. NO: 26). The result showed that a similar gene was present in all studied strains of subsp. *equi* and in a majority of strains in subsp. *zooepidemicus*.

In the following Examples 7-10, immunization and challenge of mice were performed as described below.

Bacterial strain and growth: *Streptococcus equi* subsp. *equi* was isolated from a horse with strangles. After one passage in a mouse (inoculated intranasally and reisolated from a sub-mandibular gland), the bacteria were stored at −80° C. To prepare an inoculum, stored bacteria were first grown on a blood agar plate, subcultured overnight at 37° C. in Todd Hewitt medium containing 1% (w/v) yeast extract. Six ml of this culture were taken into 50 ml of Todd Hewitt/Yeast extract medium (BBL, Becton Dickinson) containing 10% (v/v) equine, i.e. horse, serum (heat inactivated) and incubated at 37° C. for 4 hrs. Bacteria grown this way were used in animal challenge experiments.

Mice and experimental design: NMRI outbred female mice (Möllegård, Denmark) having a body weight of about 20 g, were individually marked, and kept in groups of four in each cage. Daily, they were weighed and nose impressions onto a BG plate (sheep blood and gentian violet) were taken to quantify bacterial growth. After incubation at 37° C. in 5% $CO_2$ for 24 hrs, the amount of haemolytic colonies was determined according to a scale of 0-3. A score of 3 means confluent growth of *Streptococcus* subsp *equi* on the whole plate and a score of 0 indicates 0-4 colonies.

Bronchoalveolar lavage (BAL) and nasal wash (NW) for determination of mucosal IgA responses: BAL was performed by infusing and withdrawing a solution consisting of 1 ml ice-cold PBS containing protease inhibitor (Complete, Roche) three times into the trachea. NW was performed by rinsing the nasal cavity with 0.5 ml ice-cold PBS containing protease inhibitor. The BAL and NW samples were kept on ice before storage at −80° C.

Statistical analysis: Differences between the groups were evaluated by using the Student t-test, where $p<0.05$ was considered to be statistically significant.

Example 7

Immune Response in Mice Subjected to Infection with *Streptococcus* subsp. *equi*

Figure 1:
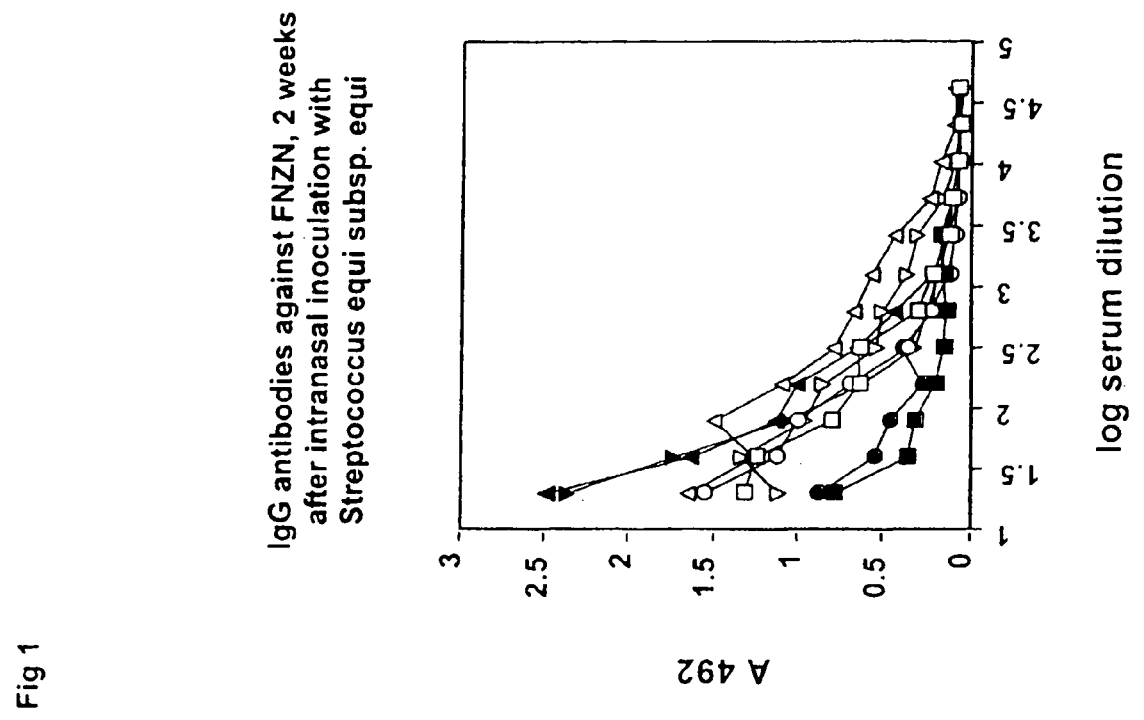
Figure 3:
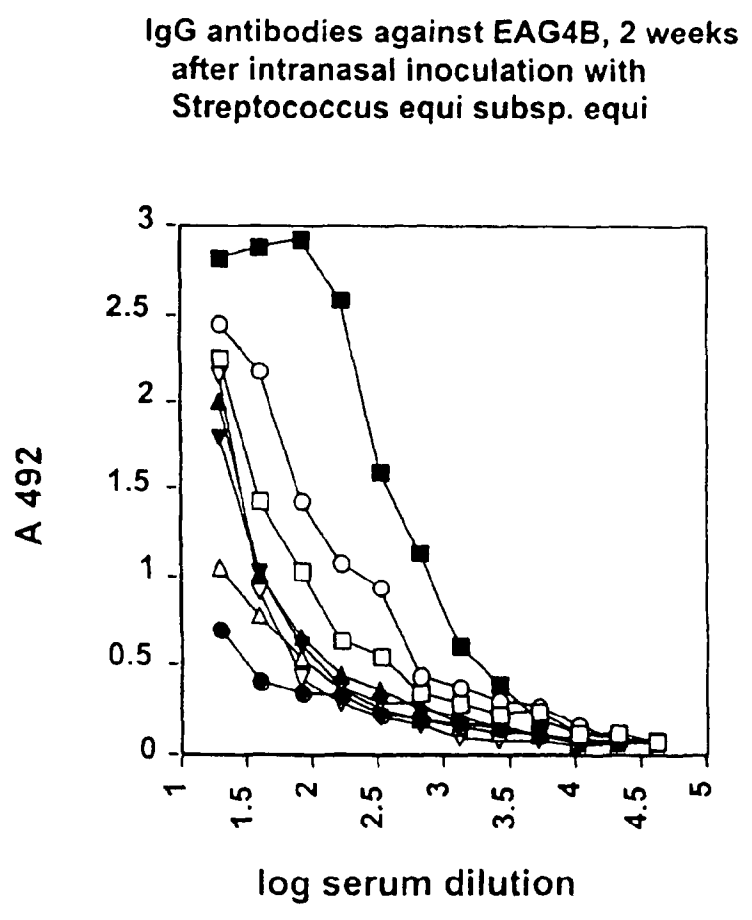

Mice (n=19) were infected with *Streptococcus* subsp. *equi*. Ten μl of bacteria containing $1 \times 10^6$ CFU were given intranasally to anaesthetized mice, viz. 5 µl in each nostril. After two weeks, the mice were sacrificed and blood samples were taken. All mice had developed IgG antibodies against FNZN, SFSC1, and EAG4B. The results from eight mice are shown in FIGS. 1, 2, and 3 for FNZN, SFSC1, and EAG4B, respectively. These ELISA tests were performed according to a standard procedure. Briefly, wells on microtiter plates (Costar) were coated with the respective proteins at a concentration of 10 µg/ml. Serum dilutions from the mice samples were applied. After washing, rabbit antibodies against mice IgG conjugated with horse radish peroxidase (Dako) were added. To develop the color reaction, OPD tablets (Dako) were added according to instructions from the manufacturer.

Example 8

Immune Response in Mice Immunized with FNZN, SFSC1, and EAG4B

Figure 5:
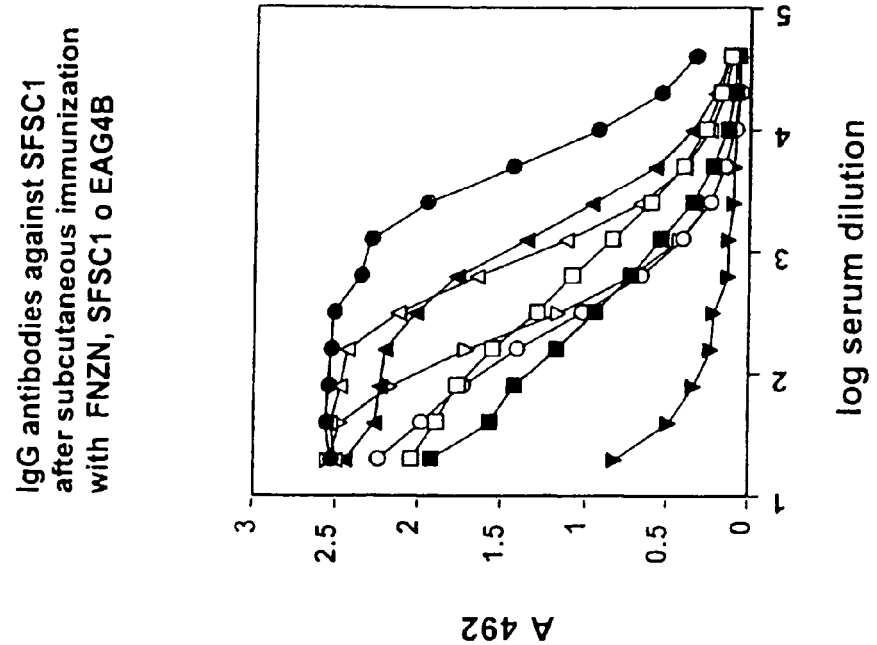
FIG. 5 shows IgG antibodies developed in mice against SFSC1 after subcutaneous immunization with FNZN, SFSC1, and EAG4B. Results obtained for seven immunized animals and one non-immunized animal (▼) are shown.
Figure 6:
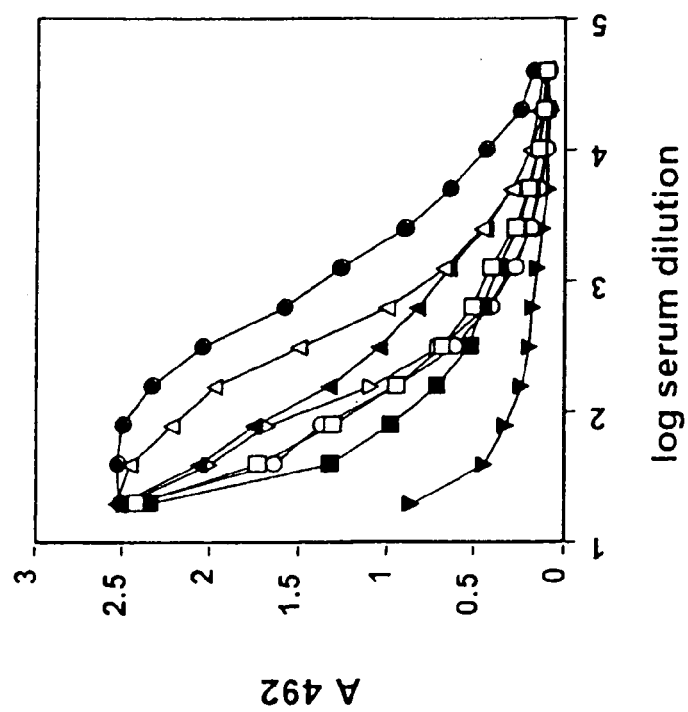
FIG. 6 shows IgG antibodies developed in mice against EAG4B after subcutaneous immunization with FNZN, SFSC1, and EAG4B. Results obtained for seven immunized animals and one non-immunized animal (▼) are shown.

Mice (n=24) were immunized subcutaneously on days 0, 7, 14, and 21. Twelve mice were given antigens (FNZN, SFSC1, and EAG4B) and adjuvant and twelve mice were given only adjutvant. The adjuvant used was EtxB provided by Dr Tim R. Hirst, University of Bristol. Each animal was given 12 µg of each antigen and 36 µg of EtxB at each occasion. On day 28, the mice were sacrificed and blood samples were taken. ELISA tests were performed as described above. All mice developed IgG antibodies against FNZN, SFSC1, and EAG4B. Samples from seven mice and a negative control are shown in FIGS. 4, 5, and 6 for FNZN, SFSC1, and EAG4B, respectively.

Example 9

Immune Response in Mice Vaccinated with SEC2.16

Figure 7:
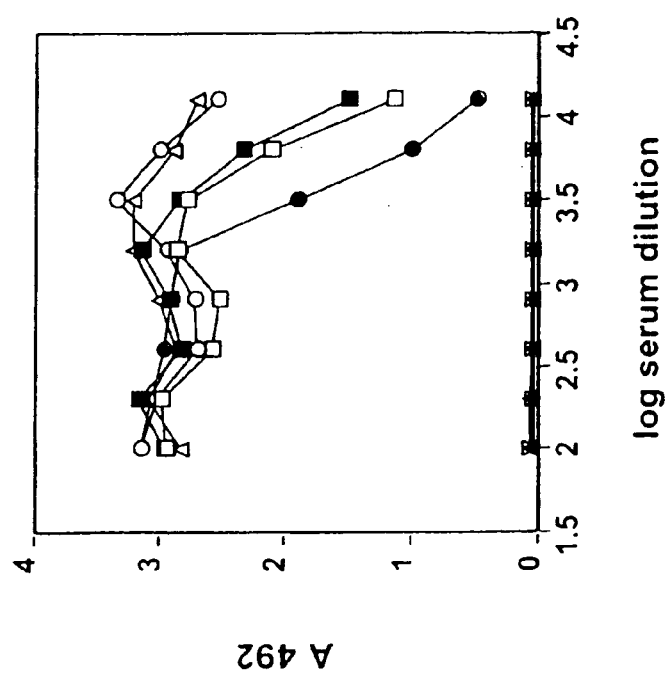
FIG. 7 shows IgG antibodies developed in mice after subcutaneous immunization with SEC 2.16. Results from five immunized and five non-immunized mice are shown. (Pre-immune sera gave no response, values closest to the base line with symbols overlapping each other).

Mice (n=5) were subcutaneously immunized on days 0, 7, 14, and 21. Each animal was given 12 µg of SEC2.16 in Freund's adjuvant. Serum samples were taken on day 28 and ELISA tests were performed as described above. In FIG. 7, the production of IgG antibodies against SEC2.16 is shown.

Example 10

Subcutaneous Immunization with FNZN, SFSC1, and EAG4B followed by Challenge with *Streptococcus equi* subsp *equi*

Mice (n=24) were subcutaneously immunized on days 0, 7, 14, and 21. Twelve mice were given antigens (FNZN, SFSC1, and EAG4B) and the adjuvant EtxB and twelve mice were given only adjuvant. Each animal was given 12 µg of each antigen and 36 µg of EtxB at each occasion. On day 28, the mice were infected with *Streptococcus equi* subsp. *equi*. Ten pi of bacteria containing $1 \times 10^6$ CFU were given intranasally to anaesthetized mice. Animals that lost more than 15% of weight were killed. Mice that had survived or had lost less than 15% of weight are shown in FIG. 8. It is evident from FIG. 8 that non-vaccinated animals had a lower survival rate than vaccinated animals. On day 3, the p-value was <0.05. From FIG. 9, it is evident that in comparison to non-vaccinated animals, fewer bacteria grew in the noses of vaccinated animals; p-values obtained on days 2, 3, and 7 are 0.03, 0.02, and 0.01, respectively.

Example 11

Intranasal Immunization with FNZN, SFSC1, EAG4B and SEC2.16 Followed by Challenge with *Streptococcus equi* subsp. *equi*

One group of mice (n=24) was intranasally immunized on days 0, 7, 14, and 21 by administration of the antigens in 40 μl as several small doses in both nostrils. Twelve mice received the antigens FNZN, SFSC1, and EAG4B together with the adjuvant EtxB and twelve mice received only the adjuvant. Each animal was given 12 μg of each antigen together with 36 μg of EtxB at each occasion. On day 28, the mice were anaesthetized and infected with *Streptococcus equi* subsp. *equi* by intranasal administration of 10 μl of bacteria containing $1\times10^6$ CFU (colony forming units).

Weight loss versus time is shown in FIG. 10; on days 2, 3, 4, 5, and 8, the p-values were 0.04, 0.017, 0.005, 0.003, and 0.002, respectively. Nasal growth versus time is shown in FIG. 11; on days 4 to 8, the p-value was <0.001. IgA antibody titers in BAL/NW and sera were determined by ELISA. Briefly, microtiter plates (Costar) were coated with 10 μg/ml of FNZN, SFSC1, and EAG4B. Serial dilutions of BAL/NWs were added to the wells. After washing, goat anti mouse IgA conjugated with horse radish peroxidase (Dako) was added. To develop the color reaction, OPD tablets (Dako) were added. From FIG. 12 it is evident that BAL/NW samples from the animals contained IgA. Moreover, IgA against SFSC1 and EAG4B was also found in serum samples from some of the animals (data not shown).

Another group of mice (n=15) was immunized intranasally with SEC2.16 using Matrix (Ref. 20) as adjuvant and a control group was given the Matrix adjuvant alone (n=15). The animals were subjected to challenge infection with subsp. *equi*. The number of animals that died or lost more than 15% weight were different in the two groups; five vaccinated mice and 8 non-vaccinated died (FIG. 18). This is not a statistically significant difference but is a tendency implying an effect of SEC2.16. It is likely that it would give a synergistic effect together with any or all of the other antigens mentioned above. Growth of subsp. *equi* in the noses was also studied. More bacteria were isolated from non-vaccinated mice than from vaccinated mice. On day 10, the score was 2.1 and 1.8 (on a scale from 0-3) in these groups, again implying an effect by vaccination with SEC2.16.

Example 12

Immunization of Horses

Horses with no previous history of strangles and with low antibody titers against FNZ, SFS and EAG were selected. Four groups (A-D) of horses with three horses in each group were immunized as follows: A) EAG4B, FNZN and SFSC1 with EtxB as adjuvant, and given both intranasally and subcutaneously; B) As in group A but given only intranasally; C) as in A but without EtxB as adjuvant; and D) Only EtxB, and no antigens, given both intranasally and subcutaneously. Each dose consisted of 35 μg of each antigen and 100 μg of EtxB in a volume of 2 ml for intranasal and/or subcutaneous immunization. Immunizations were given on days 0, 14, 28 and 42.

Serum samples were taken and analysed as follows: Microtiter wells (Costar) were coated overnight with 100 μl FNZN, SFSC1, or EAG4B, at 10 μg per ml overnight in phosphate buffered saline (PBS). The plates were then blocked with 2% (w/v) bovine serum albumin (BSA) for 1 hour at 37° C. After washing, horse sera were added to wells at a 20-fold dilution, followed by 2-fold serial dilutions. The plates were washed after 1 hour of incubation at 37° C. After washing, detection of antibody binding was performed with antibodies, diluted 1000×, against horse IgG, raised in rabbit and conjugated with HRP (Sigma Chemical Co). Development of a colorimetric reaction was achieved with OPD tablets (Dako, Denmark). Absorbance was determined spectrophotometrically at 492 nm.

In this way, IgG antibodies in sera of the immunized horses were determined. The results are shown in FIG. 14. The log dilution of sera required to give an absorbance at a cut off value of 1.0 was calculated for each individual serum sample. Mean values (n=3) with standard errors are shown. Samples taken before (day 0) and after (day 56) immunizations are shown. The horses were divided into four groups A) (white bars): antigens+EtxB given both s.c. and i.n.; B) (striped bars): as group A but immunization only i.n.; C) (gray bars): As in group A but omitting EtxB; D) (black bars): control group given only EtxB both i.n. and s.c.

Example 13

Determination in ELISA of Antibody Titers from Horses with or without a History of Previous Strangles Serum samples were taken from horses (n=16) without any previous or present signs of strangles, as well as from horses (n=10) with clinical signs of strangles and positive results from cultivation of *S. equi*. Microtiter wells (Costar) were coated overnight with 100 μl FNZN, SFSC1, EAG4B, SEC2.16 or SCLC1 at 10 μg per ml overnight in phosphate buffered saline (PBS). The plates were then blocked with 2% (w/v) BSA for 1 hour at 37° C. After washing, horse sera were added to wells at a 20-fold dilution, followed by 2-fold serial dilutions. The plates were washed after 1 hour incubation at 37° C. Detection of antibody binding was performed after washing, with antibodies, diluted 1000×, against horse IgG, raised in rabbits and conjugated with HRP (Sigma Chemical Co). Development of a colorimetric reaction was achieved with OPD tablets (Dako, Denmark). Absorbance was determined spectrophotometrically at 492 nm. The log 10 dilution of sera, which was required to give an absorbance at a cut-off value of 1.0, was calculated for each individual serum sample. Mean values of the log 10 dilutions, with standard errors, are shown. For comparing normal vs. strangles sera against FNZN, SFSC1, EAG4B, SEC2.16 and SCLC1, the p-values are <0.001, 0.02, <0.0001, 0.02, and <0.0001, respectively.

In FIG. 15, the results from a comparison of serum antibody titers from horses with or without strangles are shown. The designation n denotes normal horses without and the designatin s denotes horses with strangles. The log dilution of sera required to give an absorbance at a cut off value of 1.0 was calculated for each individual serum sample. Mean values with standard errors are shown. For comparing normal vs. strangles sera against FNZN, SFSC1, EAG4B, SEC2.16, and SCLC1, the p-values are <0.001, 0.02, <0.0001, 0.02 and <0.0001, respectively.

Example 14

Determination of IgA Antibody Titers from, Immunized Horses

Horses were divided into four groups (A-D) and were immunized as described in Example 12. Antigen-specific IgA in nasal wash samples from immunized horses were determined by an indirect ELISA. Monoclonal antibody K129-3E7 (2 μg/ml) against equine IgA was used to detect bound IgA in the samples followed by use of a goat anti-mouse immunoglobulin HRP conjugate (2 μg/ml). Coating concentrations of antigens were 4 μg/ml. Background values (from no-antigen plates) were subtracted. All samples were analyzed in triplicate. Antigen-specific IgA ELISA data is expressed relative to the total IgA ELISA data in order to correct for nasal secretion dilution during the nasal wash procedure. Total IgA in nasal wash samples was determined by a capture ELISA using two different monoclonal antibodies specific to equine IgA. One was used to coat wells and the other was biotinylated and was detected with the use of a streptavidin-HRP conjugate. The concentrations of monoclonal antibody and streptavidin-HRP were optimized so that none of these was limiting in the assay. Samples were analysed in triplicate. In FIG. 16, the Absorbance values obtained for IgA against FNZN and EAG4B are shown.

In FIG. 16, IgA antibodies in nasal washings of immunized horses are shown. Mean absorbance values (n=3) in ELISA from groups A-D are shown. The horses were divided into four groups; A) antigens+EtxB given both s.c. and i.n.; B) as group A but immunization only i.n.; C) as in group A but omitting EtxB; D) control group given only EtxB both i.n. and s.c. Light gray bars: samples from day 0 and dark gray bars from day 56.

Example 15

Determination of Kinetics for Development of IgG in Immunized Horses

Horses were immunized as described in Example 12. On days 0, 14, 28 and 42, samples were taken on these days and on day 56 as well and analyzed as described elsewhere. The horses were immunized with EAG4B, FNZN and SFSC1 with EtxB, by both intranasal and subcutaneous route.

The antibody titers against EAG4B found in these (three) horses are shown in FIG. 17 as a function of time.

Example 16

Immunogenicity of Protein SEC

Mice were immunized intranasally with SEC2.16, with (n=5) or without Matrix (n=5) using 20 μg per mouse of both SEC2.16 and Matrix. Serum samples were taken before and after 4 immunizations, with two-week intervals between. Pre-immune sera did not contain any detectable antibodies against SEC2.16. SEC2.16 without any adjuvant gave significant antibody responses in absence of Matrix. In presence of Matrix even better antibody titers were obtained as shown in FIG. 19.

Example 17

Comparison of Immunization with Different Antigens Followed by Challenge Infection Mice were immunized with proteins FNZN+SFSC1+EAG4B with EtxB (n=8) or with EAG4B with EtxB (n=10) as described in Example 11. Another group was given EtxB alone as control (n=9). The mice were subjected to challenge with subsp. *equi* and their weight change was monitored. As expected, the control group lost more weight than the groups that were given antigen, which confirms the protective effect of vaccination. The infected mice were left for 14 days. Animals in the group, which was given FNZN+SFSC1+EAG4B with EtxB as adjuvant regained weight from day 10, when average weight loss was approx. 10%, whereas on day 14, average loss was 7%. On the other hand, mice vaccinated with EAG4B with EtxB as adjuvant, kept loosing weight and on day 14 weight loss in this group was 12.5%. The difference in weight loss on day 14 implies that supplying EAG4B together with other antigens, such as SFSC1 and/or FNZN improves protection. However, the difference is not significant due to small sample size. (No data shown)

REFERENCES

1. Courtney, H. S., Y. Li, J. B. Dale, and D. L. Hasty. 1994. Cloning, sequencing and expression of a fibronectin/fibrinogen-binding protein from group A streptococci. Infect. Immun. 62:3937-3946.
2. Cue, D., P. E. Dombek, H. Lam, and P. P. Cleary. 1998. *Streptococcus pyogenes* serotype M1 encodes multiple pathways for entry into human epithelial cells. Infect. Immun. 66:4593-4601.
3. Barnbam, M., A. Ljunggren, and M. McIntyre. 1987. Human infection with *Streptococcus zooepidemicus* (Lancefield group C): three case reports. Epidem. Inf.98; 183.-190
4. Galán, J. E., and J. F. Timoney. 1988. Immunologic and genetic comparison of *Streptococcus equi* isolates from the United States and Europe. J. Clin. Microbiol. 26:1142-1146.
5. Hynes, T. O. 1990. Fibronectins. Springer Verlag, New York.
6. Engvall, E., E. Ruoslahti, and J. M. Miller. 1978. Affinity of fibronectin to collagen of different genetic types and to fibronogen. J. Exp. Med. 147:1584-1595.
7. Patti, J. M., Jonsson, H., Guss, B., Switalski, L. M., Wiberg, K, Lindberg, M., and Höök, M. (1992) Molecular characterization and expression of a gene encoding a *Staphylococcus aureus* collagen adhesin. *J. Biol. Chem.* 267:4766-4772.
8. Jonsson, H., Lindmark, H., and Guss. B. (1995) A protein G related cell surface protein in *Streptococcus zooepidemicus*. Infect Immun 63:2968-2975.
9. Lindmark, H., Jacobsson, K, Frykberg, L., and Guss, B. (1996) Fibronectin-binding protein of *Streptococcus equi* subspecies *zooepidemicus*. Infect Immun 64:3993-3999.
10. Jacobsson, K, Jonsson, H., Lindmark, H., Guss, B., Lindberg, M., and Frykberg. L. (1997) Shot-gun phage display mapping of two streptococcal cell-surface proteins. *Microbiol Res.* 152:1-8.
11. Lindmark, H., Jonsson, P., Olsson-Engvall, E., and Guss, B. (1999) Pulsed-field gel electrophoresis and distribution of the genes zag and fnz in isolates of *Streptococcus equi*. Res Vet Sci. 66:93-99.
12. Lindmark, H., and Guss, B. (1999) SFS, a novel fibronectin-binding protein from *Streptococcus equi*, inhibits the binding between fibronectin and collagen. Infect. Immun. 67: 2383-2388.
13. Lindmark, H. (1999) Characterization of adhesive extracellular proteins from *Streptococcus equi*. (Doctoral thesis) Acta Universitatis Agriculturae Sueciae, Agraria 139. ISBN 91-576-5488-3
14. Lindmark, H., Nilsson, M., and Guss, B. (2001) Comparison of the fibronectin-binding protein FNE from *Streptococcus equi* subspecies *equi* with FNZ from *S. equi* subspecies *zooepidemicus* reveals a major and conserved difference. 69: 3159-3163.
15. Schneewind, O., Fowler, A. and Faull, K. F. (1995) Structure of the cell wall anchor of surface proteins in *Staphylococcus aureus*. Science 268:103-106.
16. Anton Mayr et al. Handbuch der Shutzimpfungen in der Tiermedizin.3.3.4. p. 196-200. Verlag Paul Parey. Berlin and Hamburg. 11984
17. Elson, C. O., and M. T. Dertzbaugh. 1999. p. 817-838, Nucosal immunology, $2^{nd}$ ed. Of Academic Press, New York, N.Y.
18. Winner et al. 1991. Infect. Immun. 59:997-982
19. Ogra et al. Clinical Microbiology Reviews, April 2002, p. 430-445.
20. B. Morein and Karin Lövgren Bengtsson 1998, 76:295-299. Immunology and Cellbiology
21. Hanski, E., and M. G. Caparon. 1992. Protein F, a fibronectin-binding protein, is an adhesin of the group A streptococcus *Streptococcus pyogenes*. Proc. Natl. Acad. Sci. USA 89:6172-6176.
22. Hanski, E., P. A. Horwitz, and M. G. Caparon. 1992. Expression of protein F, the Fibronectin-binding protein of *Streptococcus pyogenes* JRS4, in heterologous streptococcal and enterococcal strains promotes their adherence to respiratory epithelial cells. Infect. Immun. 60:5119-5125.
23. Jadoun, J., V. Ozeri, E. Burstein, E. Skutelsky, E. Hanski, and S. Sela.1998. Protein F1 required for efficient entry of *Streptococcus pyogenes* into epithelial cells. J. Infect. Dis. 178:147-158.
24. Molinri, G., S. R. Talay, P. Valentin-Weigand, M. Robde, and G. S. Chhatwal. 1997. The fibronectin-binding protein of *Streptococcus pyogenes* SfbI, is involved in the internalization of group A streptococci by epithelial cells. Infect. Immun. 65:1357-1363.
25. Lannergård, J., Frykberg, L. and Guss B. (2003) CNE, a collagen-binding protein of Streptococcus equi. FEMS Microbiol. Lett. 222:69-74
26. WO 92/07002
27. WO 00/37496

The invention claimed is:

1. An isolated antigenic composition comprising:
   (i) a first antigen comprising
       SEQ ID NO:1,
   (ii) a second antigen comprising
       the amino acid sequence set forth as amino acids 2-303 in SEQ ID NO:22 or the amino acid sequence set forth as amino acids 2-590 in SEQ ID NO:20, and
   (iii) a third antigen comprising
       the amino acid sequence set forth as amino acids 2-233 in SEQ ID NO:27.

2. The isolated antigenic composition of claim 1,
   wherein said first antigen consists of SEQ ID NO: 1
   wherein said second antigen consists of the amino acid sequence set forth as amino acids 2-303 in SEQ ID NO:22
   and wherein said third antigen consists of the amino acid sequence set forth as amino acids 2-233 in SEQ ID NO:27.

3. The isolated antigenic composition of claim 1,
   wherein said second antigen comprises the amino acid sequence set forth as amino acids 2-590 in SEQ ID NO:20.

4. The isolated antigenic composition of claim 1,
   wherein said third antigen consists of the sequence set forth as amino acids 2-233 in SEQ ID NO: 27.

5. The isolated antigenic composition of claim 1,
   further comprising at least one further antigen (iv), said further antigen (iv) comprising a protein selected from the group consisting of
   (a) an isolated protein designated FNZ comprising the amino acid sequence of SEQ ID NO:2 or an N-terminal fibronectin-binding part of FNZ comprising the amino acid sequence of amino acids 4-309 in SEQ ID NO:13, and
   (b) an isolated protein designated SFS comprising the amino acid sequence of SEQ ID NO: 3 or a part of SFS comprising the amino acid sequence of amino acids 2-121 in SEQ ID NO:10.

6. An immunizing composition, which comprises the antigenic composition of claim 1 as an immunizing component, and a pharmaceutically acceptable carrier.

7. The immunizing composition of claim 6, which further comprises an adjuvant.

8. The immunizing composition of claim 6, which is provided in a physiologically administrable form and is administrable by subcutaneous or intranasal inoculation.

9. The immunizing composition of claim 6 which reduces severity of S. equi infection in non-human mammals.

10. A method for preparation of an immunizing composition for immunizing non-human mammals against infection of Streptococcus equi, which immunizing composition contains the antigenic composition of claim 1, which antigenic composition comprises antigens, which antigens are prepared in accordance with a method comprising the following steps:
    (a) providing a DNA fragment encoding said antigen and introducing said fragment into an expression vector;
    (b) introducing said vector, which contains said DNA fragment, into a compatible host cell;
    (c) culturing said host cell provided in step (b) under conditions required for expression of the antigen encoded by said DNA fragment; and
    (d) isolating the expressed antigen from the cultured host cell, and, optionally,
    (e) purifying the isolated product from step (d) by chromatography and
    mixing said antigenic composition with a pharmaceutically acceptable carrier.

11. The method according to claim 10, wherein said chromatography is affinity chromatography.

12. A method for preparation of an immunizing composition, which contains as immunizing component, an antigenic composition of claim 1, said method comprising mixing said antigenic composition and a pharmaceutically acceptable carrier.

13. A method of immunizing or therapeutic treatment of S. equi infection in non-human mammals, comprising administering to said mammal the immunizing composition of claim 6.

14. The method of claim 13, where the non-human mammals are horses.

15. A method for immunizing horses against Streptococcus equi infection, which comprises inoculating a horse with the immunizing composition of claim 6 to induce an immune response against Streptococcus equi in said horse.

16. The method of claim 15, wherein the horse is inoculated subcutaneously or intranasally.

17. The method of claim 15, wherein an immune response in the form of IgG and/or IgA and/or IgM antibodies in the nasopharyngeal mucus is induced in said horse.

18. Monoclonal antibodies against antigen(s) of the composition of claim 1.

19. A method for the production of an antiserum, said method comprising administering an antigenic preparation of claim 1 to an animal host to produce antibodies in said animal host and recovering antiserum containing said antibodies produced in said animal host.

20. A method of prophylactic or therapeutic treatment of S. equi infection in non-human mammals, comprising administering to said mammal an immunologically effective amount of an antiserum produced according to claim 19.

* * * * *